(12) United States Patent
Matich

(10) Patent No.: US 10,646,676 B1
(45) Date of Patent: May 12, 2020

(54) CPAP LIVING SEAL

(71) Applicant: Breathe Safely, Inc., Baxter, MN (US)

(72) Inventor: Ronald D. Matich, Baxter, MN (US)

(73) Assignee: Breathe Safely, Inc., Baxter, MN (US)

( * ) Notice: Subject to any disclaimer, the term of this patent is extended or adjusted under 35 U.S.C. 154(b) by 747 days.

(21) Appl. No.: 15/299,253

(22) Filed: Oct. 20, 2016

Related U.S. Application Data

(60) Provisional application No. 62/323,598, filed on Apr. 15, 2016, provisional application No. 62/244,733, filed on Oct. 21, 2015.

(51) Int. Cl.
 *A61M 16/06* (2006.01)
 *A61M 16/00* (2006.01)
 *A61L 31/12* (2006.01)

(52) U.S. Cl.
 CPC ......... *A61M 16/0605* (2014.02); *A61L 31/12* (2013.01); *A61M 16/0066* (2013.01); *A61M 16/0666* (2013.01); *A61M 16/0683* (2013.01); *A61M 2016/003* (2013.01); *A61M 2016/0027* (2013.01)

(58) Field of Classification Search
 CPC .............................................. A61M 16/0605
 See application file for complete search history.

(56) References Cited

U.S. PATENT DOCUMENTS

| | | | |
|---|---|---|---|
| 2,798,053 A | 7/1957 | Brown | |
| 4,509,949 A | 4/1985 | Huang et al. | |
| 4,599,379 A | 7/1986 | Flesher et al. | |
| 4,628,078 A | 12/1986 | Glover et al. | |
| 4,835,206 A | 5/1989 | Farrar et al. | |
| 4,849,484 A | 7/1989 | Heard | |
| 5,017,605 A | 5/1991 | Stindl | |
| 5,087,445 A | 2/1992 | Haffey et al. | |
| 5,100,660 A | 3/1992 | Hawe et al. | |
| 5,362,488 A | 11/1994 | Sibley et al. | |
| 5,704,345 A | 1/1998 | Berthon-Jones | |
| 5,746,201 A | 5/1998 | Kidd | |
| 5,798,108 A | 8/1998 | Nadaud et al. | |
| 6,029,665 A | 2/2000 | Berthon-Jones | |
| 6,123,071 A | 9/2000 | Berthon-Jones et al. | |
| 6,172,247 B1 | 1/2001 | Copeland et al. | |
| 6,262,330 B1 | 7/2001 | Fujisawa et al. | |
| 6,297,421 B1 | 10/2001 | Kitazaki et al. | |
| 6,346,256 B1 | 2/2002 | Simon | |
| 6,595,215 B2 | 7/2003 | Wood | |
| 6,776,162 B2 | 8/2004 | Wood | |
| 6,807,967 B2 | 10/2004 | Wood | |
| 7,017,577 B2 | 3/2006 | Matich | |
| 7,758,851 B2 | 7/2010 | Urgell Beltran et al. | |
| 7,887,788 B2 | 2/2011 | De La Poterie et al. | |
| 8,381,727 B2 | 2/2013 | Matich | |
| 8,573,217 B2 | 11/2013 | Todd et al. | |
| 8,752,551 B2 | 6/2014 | Chandran et al. | |
| 8,807,139 B1 | 8/2014 | Kostrzewski | |
| 8,828,410 B2 | 9/2014 | Sakuta | |
| 9,084,863 B2 | 7/2015 | Ho et al. | |
| 9,272,108 B2 | 3/2016 | Hu | |
| 2005/0191262 A1 | 9/2005 | De La Poterie et al. | |
| 2005/0199240 A1 | 9/2005 | Hall | |
| 2009/0293875 A1 | 12/2009 | Kwok et al. | |

OTHER PUBLICATIONS

"Easy Comforts" (https://www.easycomforts.com/buy-cpap-gel-mask-leak-sealer-4-oz-358366) accessed Jun. 25, 2019, pp. 1-2. ( Year: 2019).*
"Amazon" (https://www.amazon.com/CPAP-Gel-Mask-Leak-Sealer/product-reviews/B00AZLM6JM/ref=cm_cr_getr_d_paging_btm_next_9?ie=UTF8&reviewerType=all_reviews&sortBy=recent&pageNumber=9) Apr. 4, 2013, pp. 1-2. ( Year: 2013).*
cpapbeardseal.com, CPAP Beard Seal, webpage at https://www.cpapbeardandmustacheseal.com/shop/ on Oct. 29, 2016.

* cited by examiner

*Primary Examiner* — Andrew S Rosenthal

(57) ABSTRACT

A present disclosure includes a) a method for sealing a face mask to a face with a facial cream, b) a method for cleaning a human face having a face mask sealant thereon that includes the step of rubbing the face mask sealant into the face, and c) a face mask sealant composition that is applied between a face mask and a human face.

25 Claims, 11 Drawing Sheets

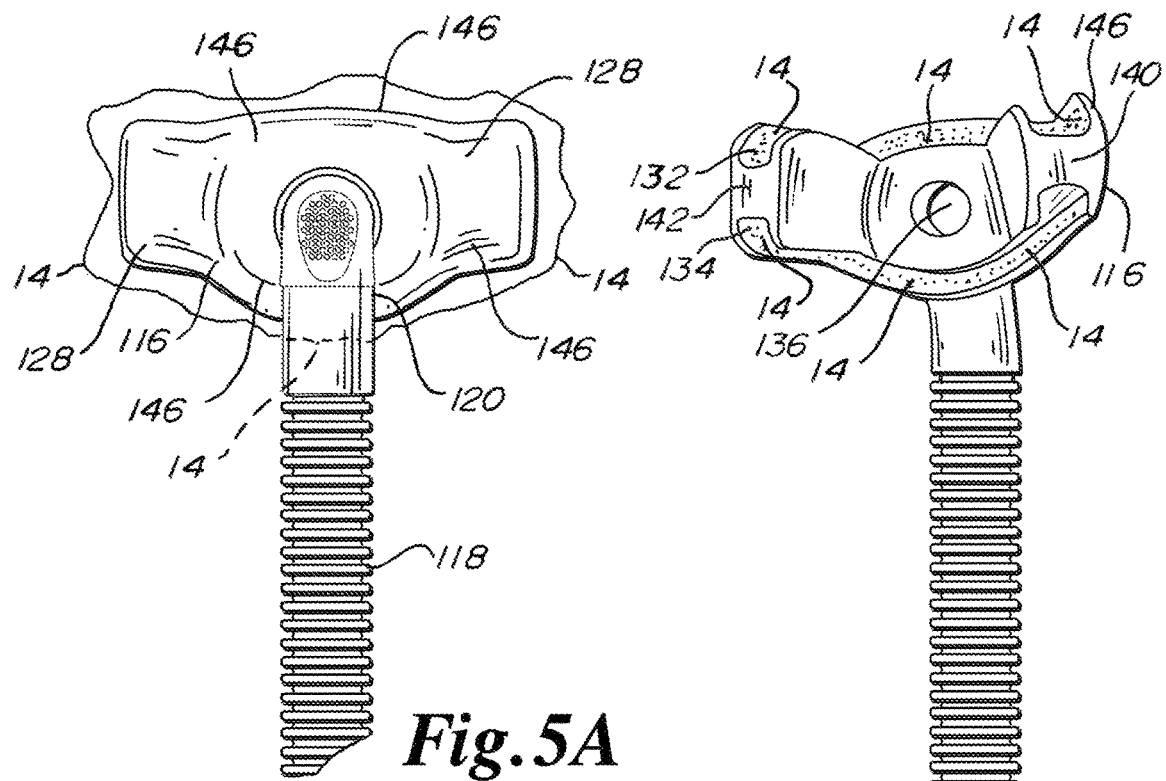
*Fig.5A*
*Fig.5B*
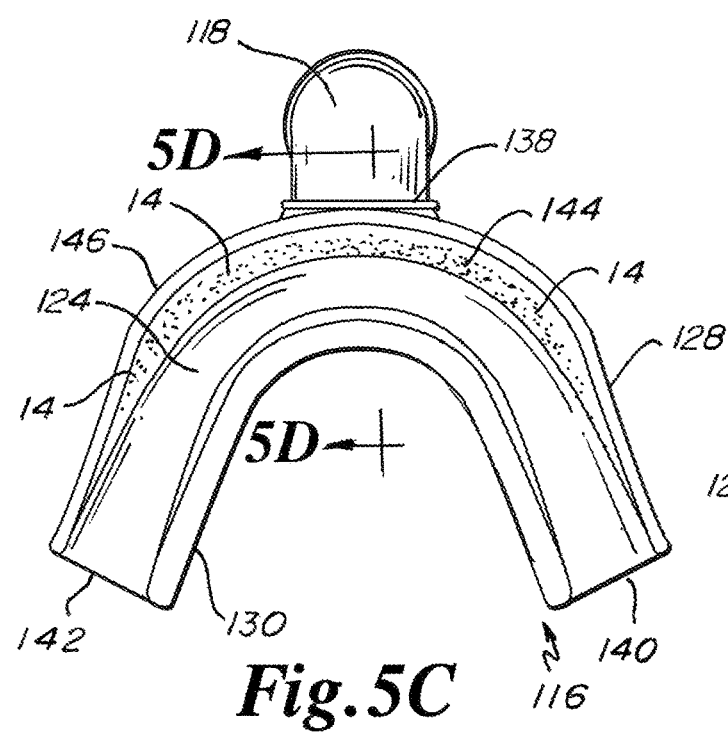
*Fig.5C*
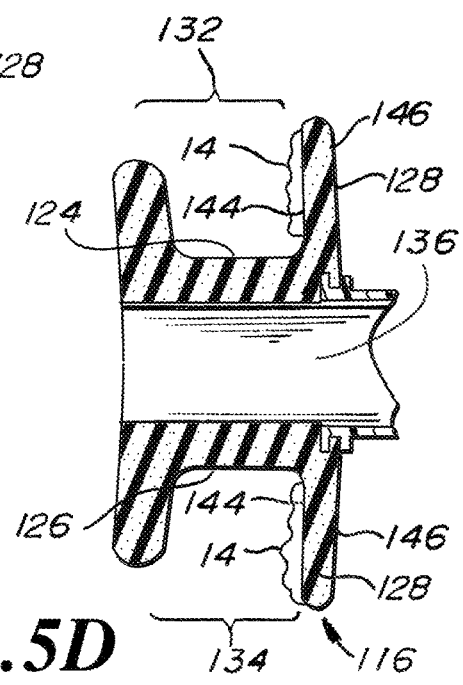
*Fig.5D* uS 10,646,676 B1

CPAP LIVING SEAL

This application claims the benefit under 35 U.S.C. 119(e) of U.S. Provisional Patent Application No. 62/244,733 filed Oct. 21, 2015 and U.S. Provisional Patent Application No. 62/323,598 filed Apr. 15, 2016, both of which applications are hereby incorporated by reference in their entireties into this application.

FIELD OF THE INVENTION

The present invention relates to topical compositions and more particularly to topical compositions that provide a living seal between a face mask or respirator and a human face.

BACKGROUND OF THE INVENTION

There are a great variety of respirators and masks that have certain peripheral structures. These certain peripheral structures are intended to fit a great variety of faces having unique noses, unique cheeks, unique cheekbones, unique mouths and unique chins. Such an intention is admirable. Such a goal is likely impossible to achieve.

CPAP is an acronym for "continuous positive airway pressure." A CPAP machine or ventilator is a continuous positive airway pressure ventilator. Such a ventilator applies mild air pressure on a continuous basis to keep the airways continuously open in a person who is able to breathe spontaneously on his or her own. Such mild pressure from a CPAP ventilator may prevent an airway from collapsing or becoming blocked.

A CPAP ventilator can be compared to a PEEP ventilator. PEEP stands for positive end-expiratory pressure. A PEEP ventilator will impose positive pressure only at the end of the exhalation. Such is in contrast to a CPAP ventilator that will apply continuous positive airway pressure throughout the breathing cycle. Each of a CPAP and PEEP ventilator "stent" the lungs' alveoli open and to recruit more of the lung's surface area for ventilation.

The CPAP ventilator itself does not cycle during CPAP. The CPAP ventilator provides no additional pressure above the level of the selected CPAP. With a CPAP ventilator, a patient must initiate all of his or her breaths. CPAP is applied without pause or end to the airway.

An adult with a relatively large face or an infant with a relatively small face may be connected to a CPAP ventilator. For example, an adult or teenager or young child with breathing issues, such as sleep apnea, may use a CPAP ventilator. Or a preterm infant or newborn may benefit from a CPAP ventilator.

CPAP "home" ventilators are sold. CPAP ventilators may include humidifiers and heated humidifiers.

CPAP masks include nasal masks, full face masks, total face masks, nasal pillow masks, hybrid masks and oral masks. A full face mask may surround only the nose and the mouth, whereas a total face mask may surround the eyes, nose and mouth. A full face mask or total face mask may be a naso-oral mask where CPAP is delivered through both the nose and the mouth.

CPAP (Continuous Positive Airway Pressure) is used to treat Obstructive Sleep Apnea (OSA) by delivering a fixed pressure of normal room air. This air pressure supports the airway by acting like an artificial splint, thereby preventing the airway from collapsing during sleep. CPAP is considered the most successful, non-invasive way of treating OSA and other sleep related breathing disorders.

CPAP users often manipulate their mask by grasping the elbow protruding from the front of the mask to use as a handle.

A common problem encountered with prior CPAP nose masks is the tendency to leak positive pressure air around the bridge and sides of the patient's nose, particularly where the cheek regions and nose intersect. This is undesirable because the continuously leaking positive pressure air tends to dry the patient's eyes, creating uncomfortable wearing and operating conditions.

SUMMARY OF THE INVENTION

A feature of the present invention is a method for creating a living seal between the peripheral structure of a face mask and a human face.

Another feature of the present invention is a method for cleaning a face after a face mask is removed from a face.

Another feature of the present invention is a composition for a facial sealant that provides a seal between the peripheral structure of a face mask or respirator and a human face.

BRIEF DESCRIPTION OF THE DRAWINGS

FIG. 5A is a front elevation view of a CPAP mouthpiece and CPAP air delivery tube from a CPAP apparatus.

FIG. 5B is a rear perspective view of the CPAP mouthpiece and CPAP air delivery tube of FIG. 5A.

FIG. 5C is a detail top view of the CPAP mouthpiece and tube of FIG. 5A.

FIG. 5D is a section view at lines 5D-5D of FIG. 5C.

DETAILED DESCRIPTION

Figure 1:
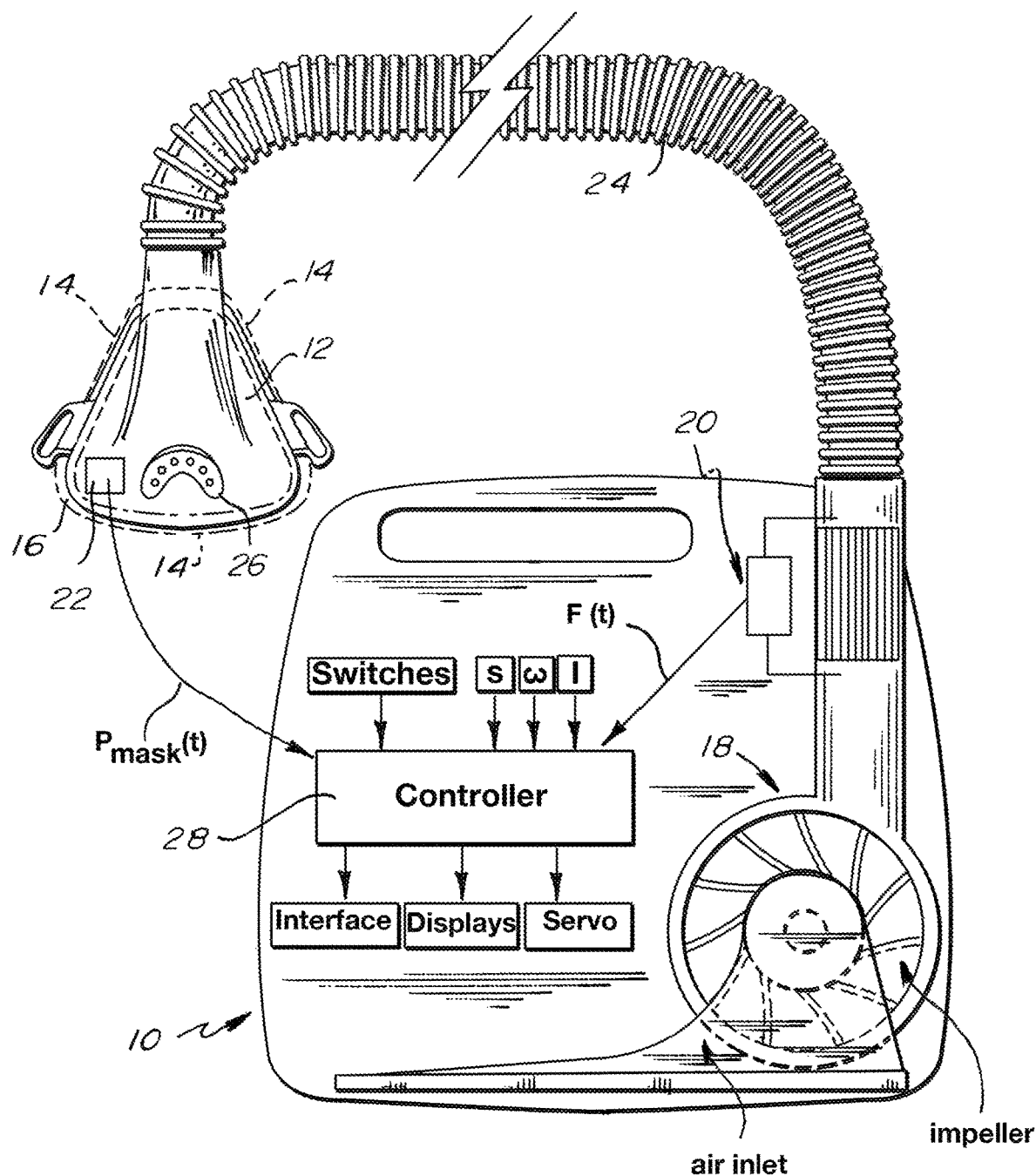
FIG. 1 is a diagrammatic view of a CPAP machine and a mouth only mask having the face cream sealant of the present invention.

A CPAP machine 10 is shown in FIG. 1. The CPAP machine 10 includes a mask 12 having the face cream sealant 14 of the present invention. This face cream sealant 14 is shown by phantom lines and is applied over an endless band shaped area on a periphery 16 of the mask 12 that confronts the face. As to the CPAP machine 10, the Kwok et al. U.S. Patent Application Publication No. US 2009/0293875 A1 published Dec. 3, 2009 and entitled Acclimatization Therapy For First Time CPAP and NIV Users is hereby incorporated by reference in its entirety.

The continuous positive airway pressure (CPAP) device 10 includes a blower 18 and blower-controller. The blower 18 can deliver a supply of air at positive pressure of 2-40 cmH$_2$O, but generally in the range of 4-20 cmH$_2$O to a patient interface via an air delivery conduit 24.

The CPAP device 10 also includes a flow sensor 20 to measure the flow of air along the air delivery conduit 24, and pressure sensors 22 to measure the pressure of air at the blower outlet on the face mask 12.

The CPAP device may include an additional pressure sensor to detect the pressure in the patient interface, such as in the face mask 12, such as between the face mask 12 and the patient's face.

The ventilator device 10, as indicated above, may include a servo-controlled blower 18, a flow sensor 20, one or more pressure sensors 22 on the mask to measure pressure inside or outside of the mask 12, the mask 12, and an air delivery conduit 24 for connection between the blower 18 and the mask 12. Exhaust gas is vented via exhaust 26.

Mask flow may be measured by a flow sensor, such as a pneumotachograph and differential pressure transducer to derive a flow signal F(t). Alternatively, the pneumotachograph may be replaced by a bundle of small tubes aligned in parallel with the flow from the blower 18 with the pressure difference measured by the differential pressure transducer across the bundle.

Mask pressure is preferably measured at a pressure tap using a pressure transducer to derive a pressure signal $P_{mask}(t)$. The pressure sensor 22 and flow sensor 20 have been shown only symbolically in FIG. 4 since it is understood that those skilled in the art would understand how to measure flow and pressure.

Flow F(t) and pressure $P_{mask}(t)$ signals are sent to a controller 28 or microprocessor 28, referred to herein as processor 28, to derive a pressure request signal $P_{Request}(t)$. The controller 28 or processor 28 is configured and adapted to perform the methodology described in more detail herein.

The controller 28 or processor 28 may include integrated chips, a memory and/or other instruction or data storage medium to implement the control methodology. For example, programmed instructions with the control methodology are either coded on integrated chips in the memory of the device or loaded as software. As those skilled in the art will recognize, analogue devices may also be implemented in the control apparatus.

The controller 28 or processor 28 is further adapted to derive parameters indicative of the patient's breathing and sleep pattern, such as for deriving indications of flow limitation, such as flow flattening, snore, apnea and hypopnea and the Apnea Hypopnea Index (AHI), and for distinguishing between REM and non-REM sleep. As to such, the Berthon-Jones U.S. Pat. No. 5,704,345 issued Jan. 6, 1998 and entitled Detection Of Apnea And Obstruction Of The Airway In The Respiratory System and the Berthon-Jones U.S. Pat. No. 6,029,665 issued Feb. 29, 2000 and entitled Determination Of Patency Of Airway are hereby incorporated by reference in their entireties.

The CPAP apparatus 10 includes other sensors, communication interfaces and displays, a servo, and functional blocks, the details of which are not necessary for an understanding of the CPAP apparatus 10.

CPAP mask 12 may be one of a number of masks, including a nasal mask, a full face mask, a total face mask, a nasal pillow mask, a hybrid mask and an oral mask. A full face mask may surround only the nose and the mouth, whereas a total face mask may surround the eyes, nose and mouth. A full face mask or total face mask may be a naso-oral mask where CPAP is delivered through both the nose and the mouth.

Figure 2A:
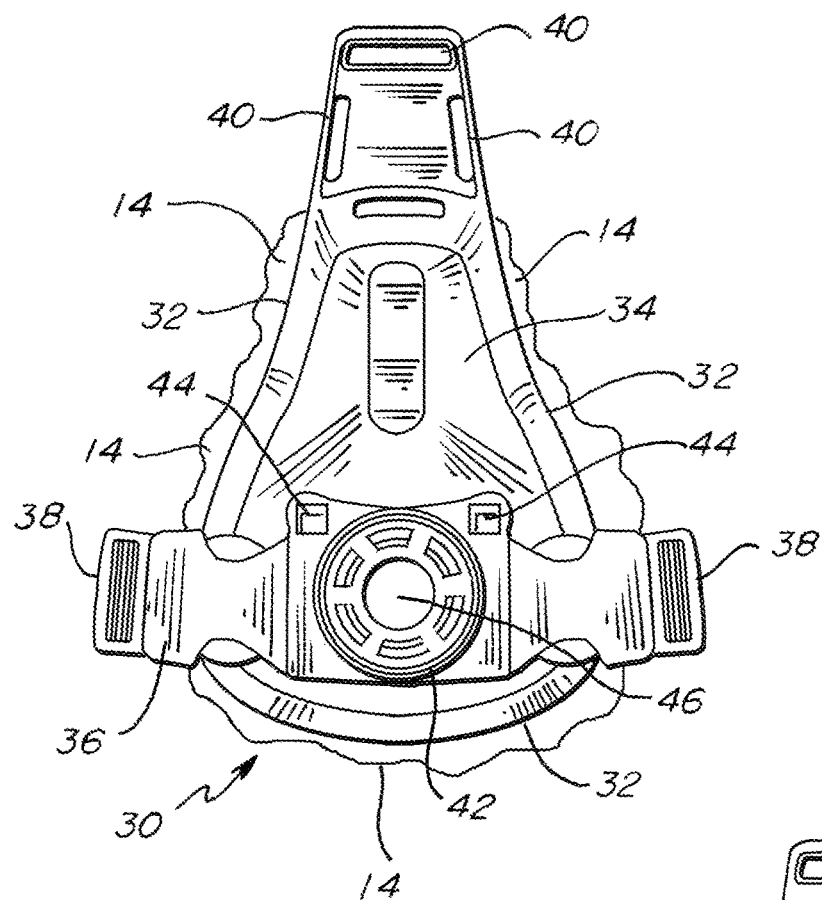
FIG. 2A illustrates a front view of a flexible CPAP full face mask.
Figure 2B:
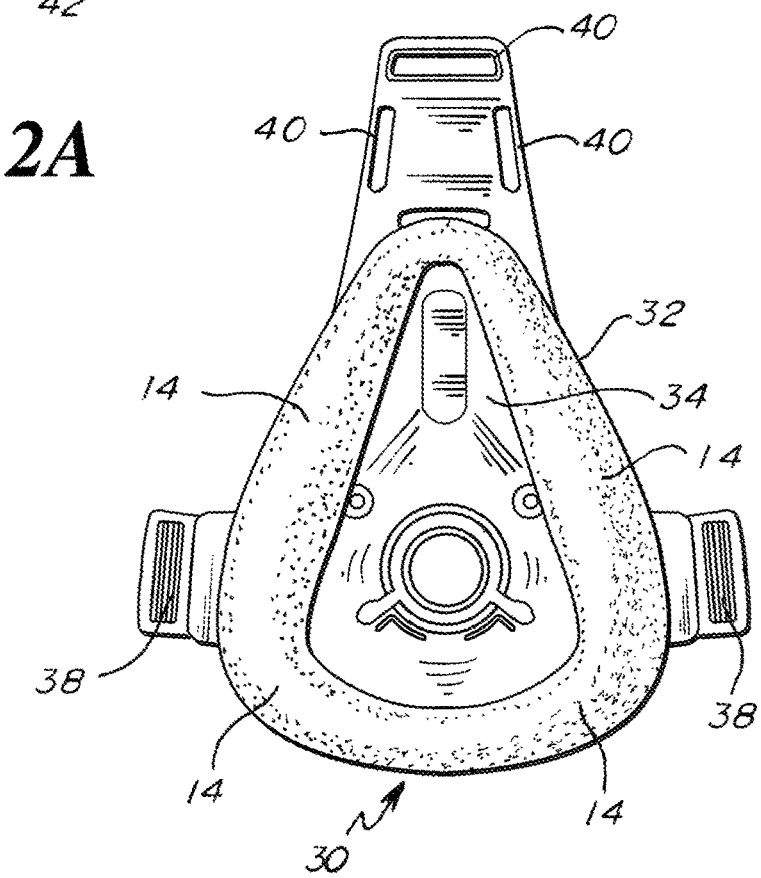
FIG. 2B illustrates a back view of the flexible CPAP full face mask of FIG. 2A.

A CPAP full face mask 30 is shown in FIGS. 2A and 2B. As to full face mask 30, the Hall U.S. Patent Application Publication No. 2005/0199240 A1 issued Sep. 15, 2005 and entitled Flexible Full-Face Mask For CPAP Treatment is hereby incorporated by reference in its entirety.

Mask 30 is a full face mask that surrounds both the nose and the mouth. Such is in contrast to a nasal mask, which covers only the nose of the patient. The nasal mask may be popular because of its small size and its asserted ability to fit a large variety of faces. However, it is not effective if the user breathes through their mouth, so numerous gadgets have been employed to assure the user's mouth is closed, such as chinstraps and lip clamps. One solution to such issues is a full-face mask, such as full face mask 30 that covers both the nose and mouth.

CPAP full-face mask 30 may be a clear, rigid shell dimensioned to cover the nose and mouth and a flexible, cushioned seal 32 for contacting the user's face. To properly fit the user, seals such as seal 32 are usually provided in a variety of sizes.

CPAP full-face mask 28 may employ a flexible shell 34 to allow a single device to comfortably fit a wide variety of users. It may employ a positionable guide wire at a periphery of the shell 34 to allow the periphery of the flexible shell 34 to be deformed to conform to the shape of a user's face.

Instead of the flexible shell 34, full face mask 30 may include a hard plastic frame.

Seal 32 may be an integrated, two-layer seal.

Mask 30, and any mask of the present invention, may be formed only of components formed of latex-free material.

The present CPAP full-face mask 30 includes a five-point harness.

FIG. 2A illustrates a front view of the present CPAP full face mask 30. FIG. 2B illustrates a back view of the flexible CPAP full-face mask 30.

The flexible shell 34 of the CPAP full-face mask 30 may be fabricated from flexible, latex-free material such as polyurethane. The result is a flexible shell that is soft and smooth to the touch. The flexibility of the shell allows both greater comfort due to a better, customized fit and increased durability due to its ability to bend to resist breakage while forming an air pressure seal.

A strap buckle 36 allows a user to easily attach head gear (not shown) or retaining straps for attaching to a mask of the present invention. Head gear or retaining straps are attached to the strap buckle 36 via attachments 38.

Additional head gear attachment points attach at the forehead strap attachment points 40. A cushion or seal 32 is attached to the shell 34 of the mask 30 and lies against the user's face. A contour wire (not shown) which is also referred to herein as a guide wire, is positioned at the inner edge of the shell 34 of the mask 30 and helps shape the shell 34 of the mask 30 to contour to multiple facial sizes and shapes, and to accommodate facial hair. A swivel assembly 42 removably attaches to the mask.

To provide a secure fit on the user, the CPAP full-face mask 30 uses a five-point harness comprising three forehead attachments 40, and two lower, side attachments 38. The shell 34 of the CPAP full face mask 30 may be molded of polyurethane. The polyurethane construction allows a bit of stretch to these attachment points 38, 40, thereby adding comfort and flexibility to the user of the full face mask 30. To ease installation and removal, the lower attachments 38 may employ a quick-release clip 36 that has large detents.

Port covers 44 cover openings for tubes that carry oxygen or other gas to the user. The port covers 44 may be shaped to have corners (i.e., shaped to be square or rectangular) or may be shaped to be rounded, such as shaped to be circular-shaped.

Full face mask 30 includes a port 46 for attaching a rigid elbow that delivers the positive airway pressure to the user. The attachment of the elbow to the port 46 in the flexible CPAP full face mask provides that the flexible CPAP full face mask will absorb forward or lateral force applied to the elbow without causing displacement of the flexible CPAP full face mask 30 to the same degree that occurs when the same degree of forward or lateral force is applied to an elbow attached to a rigid CPAP full face mask. However, if desired, full face mask 30 may have a rigid shell 34 such that CPAP full face mask 30 may be a rigid CPAP full face mask.

A rear or back view of the CPAP full face mask 30 is illustrated in FIG. 2B. This is the side or face of the full face mask 30 that confronts or engages the face about the mouth and nose. The seal 32 may be a two layer seal, having an inner or first, silicone gel-filled portion, and an outer or second, flexible silicone portion with an open, U-shaped cross-section that "balloons" and is gently urged by the positive air pressure to form a seal against user's face, as is known in the art. The seal 32 may if desired be a foam cushion or an air-filled cushion.

The seal 32 may be integrated or permanently fixed, such as by adhesive, to the flexible shell 34 to eliminate the need for specific seal attachment structure on the shell 34. The seal 32 may be a stock replacement seal.

The flexible shell 34 of the CPAP full-face mask 30 may include a positionable contour wire also referred to as a guide wire in the peripheral portion of the shell 34 adjacent to the seal 32 to allow the periphery of the flexible shell 34 to be positioned so as to conform to the face of individual users. This "guide wire" may be a metal wire of suitable stiffness that is molded into the periphery of the shell 34.

The face cream sealant 14 of the present invention is spread to cover the portion of the seal 32 shown in FIG. 2B. The speckling in FIG. 2B shows the face cream sealant 14 of the present invention. FIG. 2A shows that the face cream sealant 14 can be spread beyond the seal 32, such that, if a patient self adjusts the full face mask 30 during the night, chances are maximized that a seal between the face of the user and the full face mask 30 will still be present.

Figure 3A:
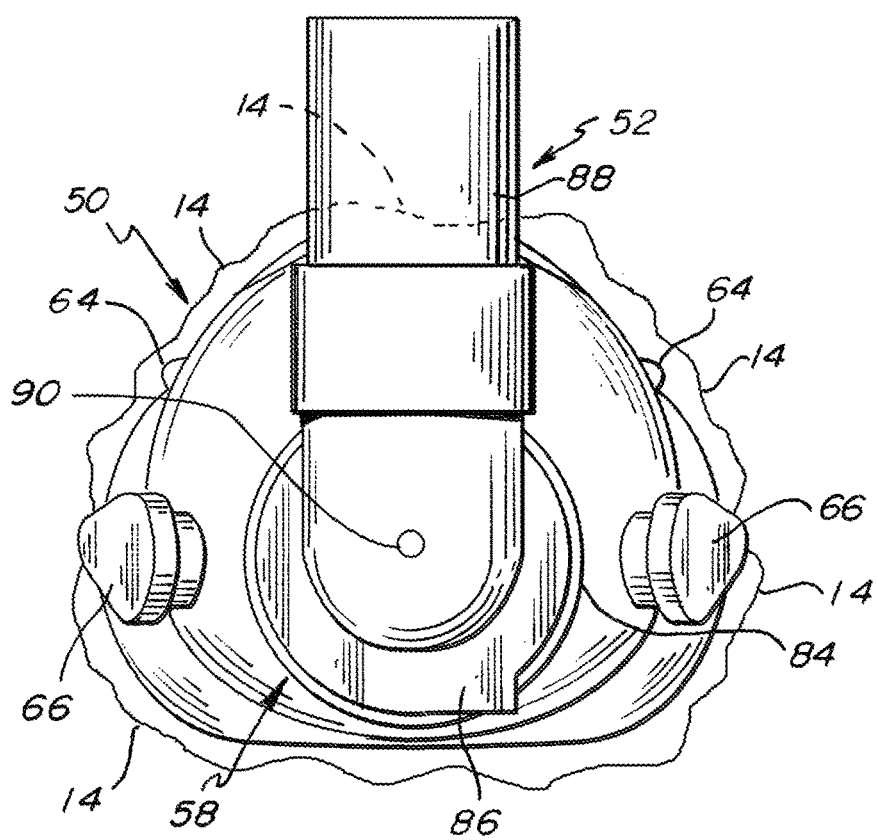
FIG. 3A is a front end view of a CPAP nose mask and an air source fitting.
Figure 3B:
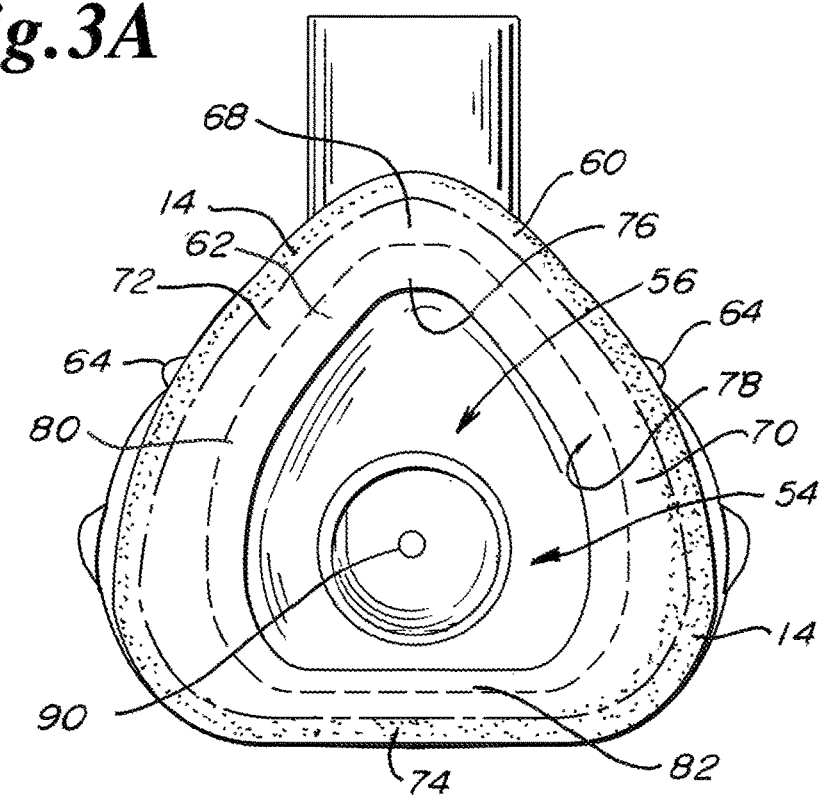
FIG. 3B is a rear end view similar to that of FIG. 3A, but depicting the opposite end of the CPAP nose mask and showing in detail a nose entrance opening.

A CPAP nose or nasal mask 48 is shown in FIGS. 3A and 3B. As to the CPAP nose or nasal mask 48, the Kidd U.S. Pat. No. 5,746,201 issued May 5, 1998 and entitled CPAP Nose Mask is hereby incorporated by reference in its entirety.

The CPAP nose mask 48 includes a soft, resilient, synthetic resin body 50 and an air source connection fitting 52. The body 50 presents an internal nose-receiving cavity 54 as well as a generally triangular nose entrance opening 56 and a spaced, opposed, inhale/exhale opening 58. The openings 56, 58 are in communication with the cavity 54. The entrance opening 56 is defined by a circumscribing flange 60 and an inboard, pliable, inwardly extending, sealing lip 62. A metallic, deformable, shape-retaining reinforcing member 64 is secured to the outer surface of the flange 60 and extends over the bridge and sidewall regions of the flange 60. The member 64 can be readily shaped so as to accommodate the shape and contour of the user's nose and face. Member 64 is an external, metallic, manually deformable, and shape-retaining reinforcing bridge element that permits custom shaping of the upper margin of the nose mask 48 to fit the particular nose configuration of the user.

The nose mask 48 is in the form of a hollow body of integral construction and formed of a synthetic resin such as silicone rubber. The nose mask 48 includes a wall structure defining an internal nose-receiving cavity 54, a nose entrance opening 56 and a space inhale/exhale opening 58, with the openings being in communication with the cavity 54. The nose entrance opening 56 is defined by an endless peripheral flange 60 designed to directly engage the top of the patient's nose, the sides of the nose and cheek regions adjacent the nose, and the patient's upper lip beneath the nose.

The nasal mask 48 includes a metallic, manually deformable yet shape-retaining reinforcing member 64 secured to the outer surface of the flange 60 remote from the entrance opening 56. This reinforcing member 60 is generally in the form of a strip and is located for extending over the bridge of the patient's nose and diverging downwardly along both sides of the nose. The user can readily manipulate and deform the reinforcing member 64 for shaping the nose mask 48 around the upper part of the nose and cheeks.

The inhale/exhale opening 58 of the nose mask 48 is located in opposed relationship to the nose entrance opening 56 and receives a fitting allowing connection of a positive pressure air source to the nose mask 48.

FIG. 3A is a front end view of the CPAP nose mask 48, illustrating the mask 48 and air source fitting 52.

FIG. 3B is a rear end view similar to that of FIG. 3A, but depicting the opposite end of the nose mask 48 and showing in detail the nose entrance opening 56.

The nose mask 48 includes an integral, molded, synthetic resin mask body 50 together with an interfitted positive pressure air source fitting 52. The nose mask 48 is designed to fit over the nose of a CPAP patient and be maintained in place during sleep.

The mask body 50 is preferably hollow and formed of a pliable synthetic resin material such as silicone rubber. The mask body 50 presents a somewhat triangular nose entrance opening 56 as well as an opposed inhale/exhale opening 58, the latter receiving fitting 52. A nose-receiving cavity 54 is defined by the body 50 and communicates with the openings 56, 58. The exterior surface of body 50 is also equipped with three spaced apart connection lugs 66 for connection of head straps allowing secure placement of the nose mask 48 on a patient's face.

The entrance opening 56 is defined by an endless continuous pliable peripheral flange 60 having an uppermost bridge region 68, downwardly diverging sidewall portions 70, 72 and a concave base portion 74. The flange 60 is designed to conform to the bridge and sides of the patient's nose and to the cheek regions adjacent the nose. The base portion 74 is designed to abut and engage the upper lip directly beneath the nose. The flange 60 at the upper bridge region 68 preferably has a width of approximately 0.2" and the sidewall portions 70, 72 gradually increase in width until they reach a maximum width of about 0.4" adjacent the base portion 74. The side flange portions 70, 72 then merge into and form the concave base portion 74 having a reduced vertical height of about 0.2".

The entrance opening 56 additionally includes a thin, pliable, continuous lip 62 inboard of the flange 60 and extending into the opening 56. The lip 62 has an uppermost bridge region 76 as well as diverging sidewall portions 78, 80 and a base portion 82. The region 76 and portions 78, 80 of the lip 62 have a width of approximately 0.1" and at the lower ends of the portions 78, 80 merge into the base portion 82 having a similar vertical height of around 0.1". The region 76 and sidewall portions 78, 80 of the lip 62 are relatively thin and flexible, and are thinner than the adjacent portions of the flange 60. The lower base portion 82 of the lip 62 is in effect a continuation of the base portion 74 of the flange 60, and has a thickness essentially equal to that of the flange 60.

The inhale/exhale opening 58 is circular in configuration and defined by a marginal wall 84. Fitting 52 is releasably connected to the body 50 at the region of opening 58. Fitting 14 includes a rigid synthetic resin collar 86. A two-piece L-shaped rigid synthetic resin coupler 88 is rotatably received within collar 86. The end of coupler 88 remote from collar 86 is adapted for connection to a positive pressure air line. The coupler 88 is provided with a small outlet opening 90.

In use, the nose mask 48 with fitting 52 in place is positioned over a patient's nose, usually just prior to bed time. In order to maintain the nose mask 48 in position, conventional head straps are passed over the patient's head and connected to the lugs 66. A positive pressure air line is affixed to the end of coupler 88 remote from mask body 50 for delivery of positive pressure air to the nose-receiving cavity 54. During CPAP treatment, positive pressure air is continually delivered to the nose mask 48 at a selected pressure, typically on the order of 10 cm of water. Such continuous positive pressure air has been found to ameliorate the effects of sleep apnea.

The provision of the flange 60 and lip 62 of the mask body 50 significantly enhances the seal between the mask body 50 and the patient's nose and face. It has been discovered that positive pressure air acts against the inner face of the pliable lip 62 to form a better seal, particularly along the bridge and sides of the patient's nose leading to the cheek regions. As a consequence, the nose mask 48 inhibits flow of air past the patient's nose which can cause drying of the patient's eyes. In addition, the presence of the reinforcing member 64 allows custom fitting of the nose mask 48 to the particular shape and contour of the patient's nose. As will be appreciated, the metallic member 64 can be manually bent and deformed as required to insure the most comfortable fit consistent with adequate sealing.

During the patient's breathing, positive pressure is delivered through the fitting 52. Provision of outlet opening 90 assures that the pressure within the confines of cavity 54 does not build up to an unacceptable degree, thereby causing patient discomfort or significant passage of air along the sides and bridge of the patient's nose.

The speckling in FIG. 3B shows the facial cream sealant 14. The facial cream sealant 14 is applied to at least an outer portion of the endless continuous pliable peripheral flange 60. Flange 60 includes the uppermost bridge region 68, downwardly diverging sidewall portions 70, 72 and a concave base portion 74. The facial cream sealant 14 is applied endlessly to at least about an outer half portion of the uppermost bridge region 68, to at least about an outer half portion of the downwardly diverging sidewall portion 70, to at least about an outer half portion of the downwardly diverging sidewall portion 72, and to substantially all of the concave base portion 74. The endless continuous pliable peripheral flange 60 may be defined to include base portion 82, such that the facial cream sealant 14 may, if desired, cover the entire flange 60, since downwardly diverging sidewall portions 70, 72 lead directly into each of the base portions 74, 82.

FIG. 3A shows that the facial cream sealant 14 may be spread beyond an area on the face defined by the flange 60. Patients may self adjust the nasal mask 48 such that the facial cream sealant 14 may be spread over an area larger than that defined by the flange 60 prior to placing the nasal mask 48 on the face.

FIGS. 4A, 4B, 4C and 4D, respectively, show front, side, inverted plan and rear views of a CPAP mouth mask having the present face cream sealant.

Figure 4A:
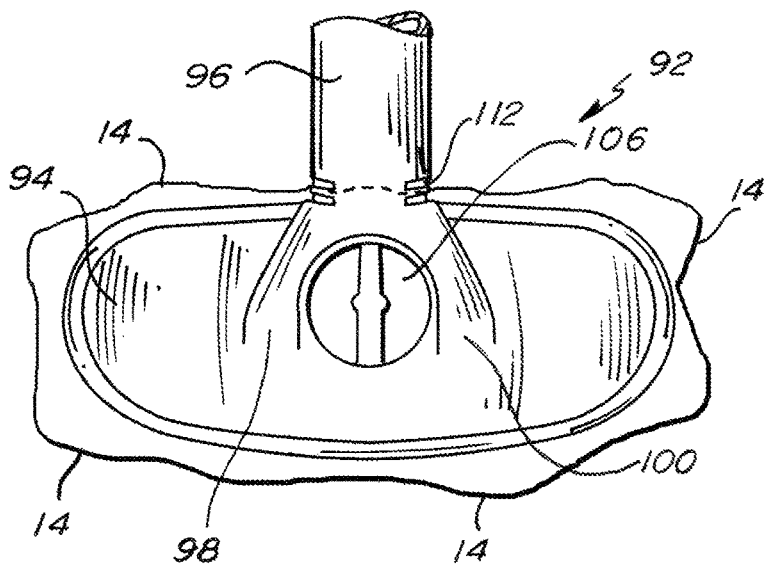
FIG. 4A shows a front view of a CPAP mouth only mask.
Figure 4B:
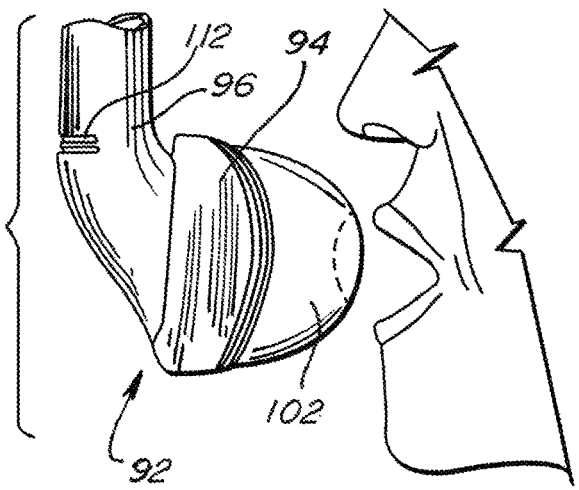
FIG. 4B shows a side view of a CPAP mouth only mask of FIG. 4A.

The mouth mask shown in FIGS. 4A and 4B is generally represented by reference numeral 92. As to CPAP mouth mask 92, the Berthon-Jones et al. U.S. Pat. No. 6,123,071 issued Sep. 26, 2000 and entitled Facial Masks For Assisted Respiration Or CPAP is hereby incorporated by reference in its entirety.

FIG. 4A is a front view of the mask 92, and FIG. 4B is a side view of the mask showing the operational relationship with the mouth of a patient to whom ventilation or CPAP is being administered.

The mask 10 comprises a flared frame or plate 94, being gently curved with rounded ends. An inlet pipe 96, which ends in two branched passageways 98, 100, is connected to the front of the plate 94. To the rear face of the frame 94 is connected a mouth cushion 102. The cushion 102 is "banana" shaped, as can be best understood from the inverted plan view of FIG. 4C and rear view of FIG. 4D. The cushion 102 defines a chamber 104, which is in communication with the branched passageways 98, 100, and, in turn, the inlet pipe 96. The closed-off end of the chamber 104, being a part of the frame 94, is provided with an optional safety valve 106, which operates to provide communication between the chamber 104 and the ambient air on there being negative pressure within the chamber 104 with respect to atmospheric pressure, such as may occur if the inlet pipe 96 becomes blocked and the patient inhales. In this regard, the valve 106 can be a conventional "flap" valve. All of the component parts, save the mouth cushion 102 and the safety valve 106, are typically constructed of a rigid plastic material.

In fitting the mouth mask 92 to a patient, the protruding end of the cushion 102 firstly comes in contact with the area surrounding the lips of the patient. The curved nature of the frame 94, together with the "banana" shape of the cushion 102 ensures that the cushion 102 completely wraps around the patient's mouth. That region around the patient's lips deforms or depresses the surface of the cushion 102 forming a continuous rolled edged seal 110 therebetween. The patient's lips are accommodated inside the opening 108 to the cushion 102.

As the rolled edge 110 of the cushion 102 is not preformed or molded into a particular shape, it forms a sealing rolled edge 110 on every occasion on which it is used, using the patient's face as a template to define the three-dimensional outline of the rolled edge. When not in use, the cushion 102 has no memory of where the rolled edge seal was previously formed, hence can adapt to different positions on the patient's face if slightly displaced, such as during sleeping. It is therefore also suitable for use by a number of different patients.

The part of the cushion 102 forming the rolled edge seal 110 can be made of a material such as molded silicone rubber of a thickness between 0.15-0.5 millimeters. Typically, the rest of the mouth cushion 102 would be formed of thicker material having the necessary resiliency so that the cushion will not completely collapse when pressed against the face of the patient, nor billow out under high mask pressures. The use of silicone material has the advantage of being sufficiently transparent to enable a patient's mouth to be observed through the mask.

It is usual to provide fastening of the mouth mask to the head of the patient by means of head straps. The head straps must be tensioned to apply a positive sealing force for the cushion 102 at all points of contact with the patient's face.

In use of the mouth mask 92, air or gas under pressure is supplied to the inlet pipe 96, typically by a motor driven pump unit and so passes to the mouth of the patient, providing the requisite positive airway pressure. The cushion 102 provides an airtight seal by virtue of the continuous rolled edge formed around the vicinity of the patient's lips. Internal air pressure acting normally on the rolled edge seal 110 against the patient's face counteracts the competing deleterious effect of this same internal pressure tending to force air out under the membrane around the inside edge of the orifice 108. This enables an airtight seal to be comfortably maintained at moderately high pressures, as may be applied in CPAP treatment or during ventilation (up to, say, 50 cm $H_2O$).

The greater the annular width of the rolled edge seal 110 around the patient's face, the less is the tendency for air to leak out of the mask. This also means that there is lesser point pressure applied to the patient's face by the tensioning head straps holding the mask in place. A further advantage of the rolled edge seal arrangement for the mouth cushion 102 is that if the mask 92 is disturbed during sleep, a seal immediately reforms along a new three-dimensional path defined by the line of contact between the area around the orifice 110 and the patient's face in the vicinity of the lips.

The mouth mask 92 can be used with the nasal passages blocked for delivery of CPAP or ventilation to a patient through the mouth. That is, there is a supply of positive air pressure, and that supplied air or gas under pressure is inspired by the patient and subsequently expired by means of the diffuser slots 112 or to another outlet to atmosphere which opens when the expired air/gas pressure exceeds atmospheric pressure.

The safety valve 106 is biased closed by a positive pressure in the mouth chamber 114 relative to the atmospheric pressure.

Figure 4C:
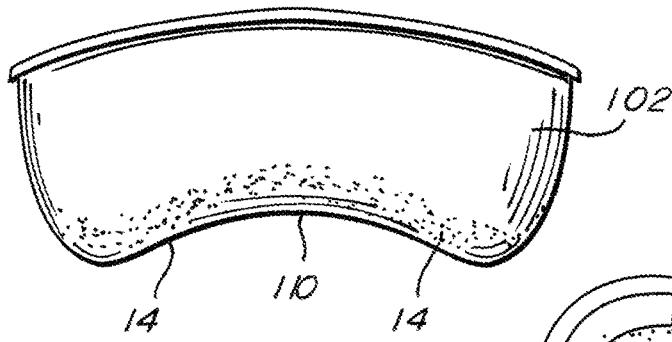
FIG. 4C shows an inverted plan view of the CPAP mouth only mask of FIG. 4A.
Figure 4D:
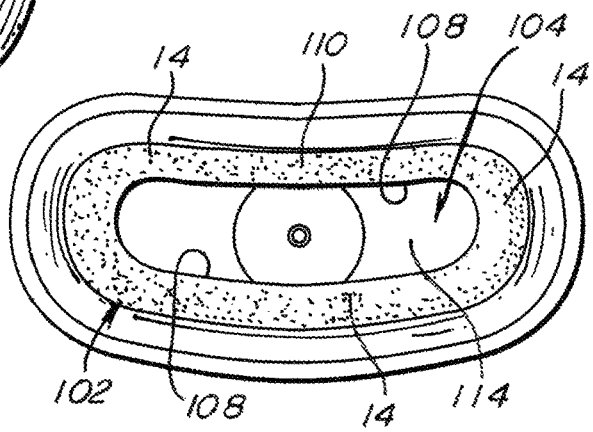
FIG. 4D shows a rear view of the CPAP mouth only mask of FIG. 4A.

The speckling in FIGS. 4C and 4D show the facial cream sealant 14. The facial cream sealant 14 is applied to at least the rolled edge seal 110 which endlessly surrounds the mouth of a person using a CPAP machine. That is, the facial cream sealant 14 is applied about the endless edge of the orifice 108 and outwardly such that an endless facial cream seal 14 is formed. The facial cream seal 14 may be spread in a wider band than shown in FIGS. 4C and 4D.

FIG. 4A shows that the facial cream sealant 14 may be spread beyond an area on the face defined by the rolled edge seal 110. Patients may self adjust the mouth mask 92 such that the facial cream sealant 14 may be spread over an area larger than that defined by the rolled edge seal 110 prior to placing the mouth mask 92 on the face.

An oral air delivery system that includes a CPAP device may include a mouthpiece 116 shown in FIGS. 5A, 5B, 5C and 5D. As to mouthpiece 116, the Kostrzewski U.S. Pat. No. 8,807,139 issued Aug. 19, 2014 and entitled Oral Air Delivery System For CPAP is hereby incorporated by reference in its entirety.

FIG. 5A is a front elevation view of CPAP mouthpiece 116 and CPAP air delivery tube from a CPAP apparatus. FIG. 5B is a rear perspective view of the CPAP mouthpiece 166 and CPAP air delivery tube of FIG. 5A. FIG. 5C is a detail top view of the CPAP mouthpiece 116 and tube of FIG. 5A. FIG. 5D is a section view at lines 5D-5D of FIG. 5C.

The mouthpiece 116 is arc-shaped and has a top surface 124, a bottom surface 126, a first side edge 128, and a second side edge 130 opposite the first side edge 128. The first side edge 128 has a longer arc length than does the second side edge 130. The first side edge 128 extends a first distance above the top surface 134 of the mouthpiece 116. The second side edge 130 extends a second distance above the top surface 124 of the mouthpiece 116. The first side edge 128 extends a third distance below the bottom surface 126 of the mouthpiece 116. The second side edge 130 extends a fourth distance below the bottom surface 126 of the mouthpiece 116. A first gap 132 exists between the portion of the first side edge 128 raised above the top surface 124 of the mouthpiece 116 and the portion of the second side edge 130 raised above the top surface 124 of the mouthpiece 116. A second gap 134 exists between the portion of the first side edge 128 extending below the bottom surface 126 of the mouthpiece 116 and the portion of the second side edge 130 extending below the bottom surface 126 of the mouthpiece 116. The first gap 132 is adapted to sandwich teeth of a user's upper jaw and the second gap 134 is adapted to sandwich teeth of a user's lower jaw. The first gap 132 and the second gap 134 are aligned on a same plane so as to align central incisors of the upper jaw and central incisors of the lower jaw. A hole 136 is disposed in the mouthpiece 116 about halfway between outer edges of the mouthpiece 116. The hole 136 is situated below the top surface 124 of the mouthpiece 116 and above the bottom surface 126 of the mouthpiece 116. The hole 136 includes a straight axis and has a height smaller than a width. The hole 136 allows passage of air from the first side edge 128 to the second side edge 130 of the mouthpiece 116. Hollow tube 118 includes a first end 120. First end 120 of the tube 118 is attached to a first end of the hole 136 via a swivel joint 138. The swivel joint 138 allows for rotation of the tube 118 with respect to the mouthpiece 116. The tube 118 includes a second end 122 that is connected to a CPAP machine, such that air can pass through the tube 118, through the hole 136 and into a user's mouth and such that air can pass from a user's mouth through the hole 136.

The speckling in FIGS. 5B and 5C show the facial cream sealant 14. The facial cream sealant 14 is applied to at least an inner face 144 of first side edge 128, where the first side edge 128 is at least partially defined by inner and outer faces 144, 146. Inner face 144 confronts the outer faces of the lips of a mouth of a person such that facial cream sealant 14 is spread upon the lips in the manner of lip balm or chapstick or lipstick is spread upon the lips. If desired, the outer edges or faces 140, 142 may also be spread with the facial cream sealant 14. These outer edges 140, 142 confront the corner portions of the lips, which corner portions lead from an outside of the mouth to an inside of the mouth.

FIG. 5D shows a layer of facial cream sealant 14 on the inner face 144 of the first side edge 128. It should be noted that first side edge 128 extends upwardly from opening 136 and depends downwardly from opening 136 such that inner face 144 is found above and below opening 136 as shown in FIG. 5D. Hence both the upper lip and lower lip of a person engages mouthpiece 116 through the face cream sealant 14 being spread upon both of the upper and lower portions of the inner face 144 of the upper and lower portions of the first side edge 128.

FIG. 5A shows that the facial cream sealant 14 may be spread beyond an area on the face defined by the periphery of the first side edge 128 of mouthpiece 116. Patients may self adjust the mouthpiece 116 such that the facial cream sealant 14 may be spread over an area larger than that defined by the first edge 128 of the mouthpiece 116 prior to placing the mouth mask 116 on the upper and lower lips of the face of a person.

Figure 6A:
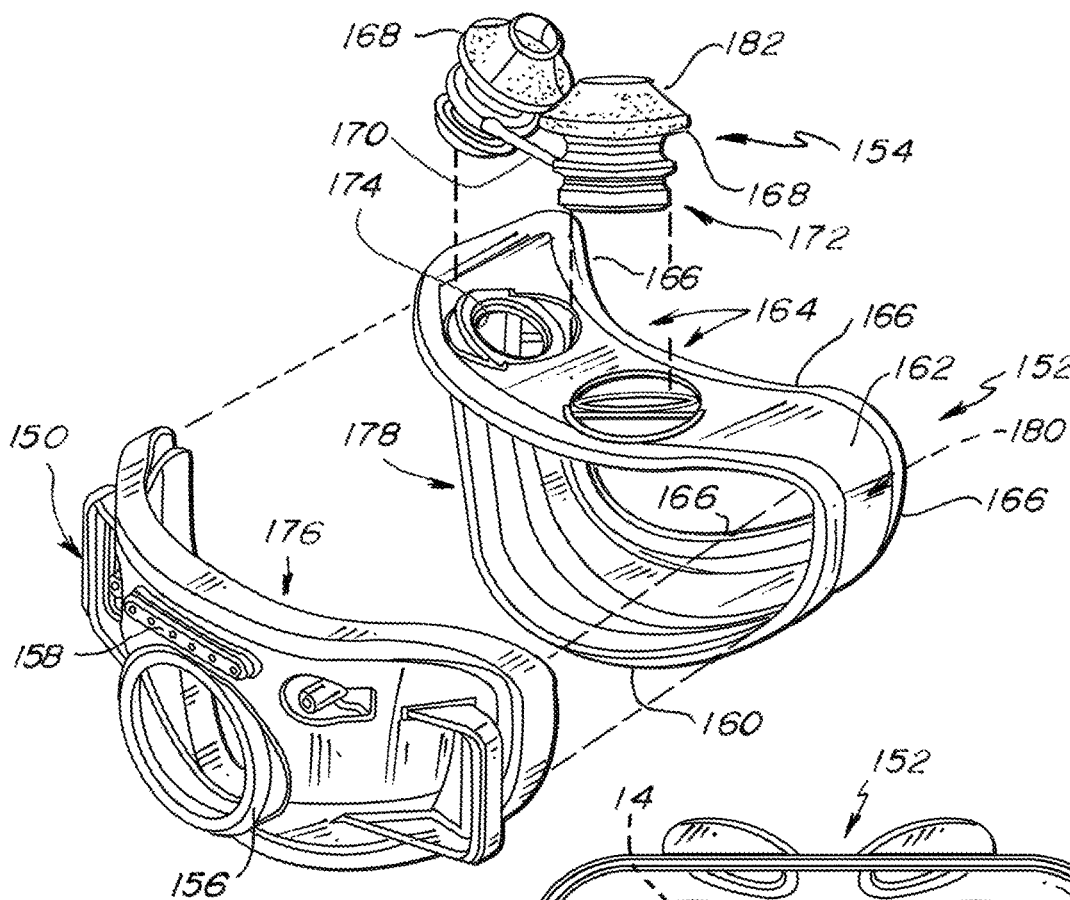
FIG. 6A is an exploded perspective view of a hybrid CPAP mask having a ventilation piece or interface, a facial piece or interface and a nasal piece or interface.
Figure 6C:
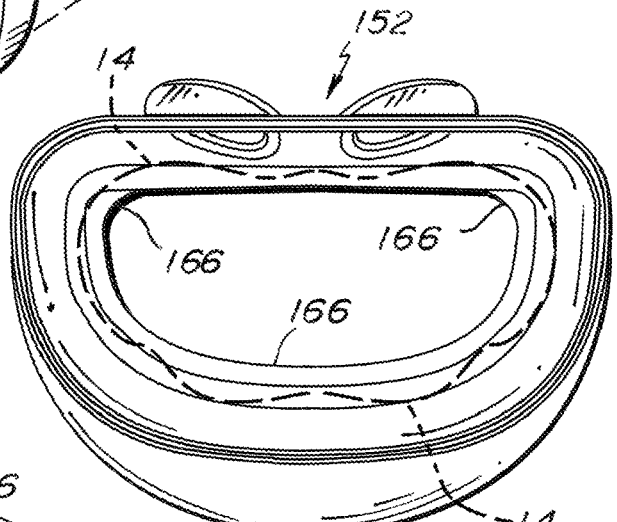
FIG. 6C is a front elevational view of the facial interface of FIG. 6B.
Figure 6B:
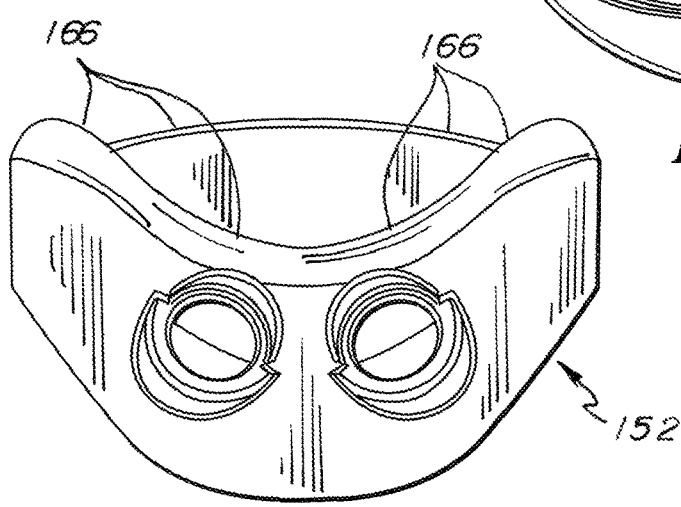
FIG. 6B is a top plan view of the facial interface portion of the hybrid mask of FIG. 6A.

FIG. 6A is an exploded perspective view of a hybrid CPAP mask having a ventilation piece or interface, a facial piece or interface and a nasal piece or interface. FIG. 6B is a top plan view of the facial interface portion of the hybrid mask of FIG. 6A. FIG. 6C is a front elevational view of the facial interface of FIG. 6B.

A hybrid mask is a mask that includes a mouth piece or portion or interface that covers only the mouth and a nasal piece or portion or interface that provide air passages to the nose. The nasal piece or portion may include a pair of nasal inserts that extend from an upper portion of the mouth interface to the nostrils. The hybrid mask provides continuous positive air pressure (CPAP) to both the mouth and nose at the same time.

FIGS. 6A, 6B, and 6C show a hybrid mask 148. The hybrid mask 148 through a CPAP machine provides positive air pressure to a person and generally includes three parts: a ventilation interface 150, a cushioned facial interface 152, and a nasal interface 154. As to the hybrid face mask 148, the Chandran et al. U.S. Pat. No. 8,752,551 issued Jun. 17, 2014 and entitled Hybrid Ventilation Mask With Nasal Interface And Method For Configuring Such A Mask is hereby incorporated by reference in its entirety.

The hybrid mask 148 completely covers only the mouth of the user. Nonetheless, the hybrid mask 148 is still fluidically coupled to the nostrils of the user through the nasal interface 154. As such, the hybrid mask 148 regulates breathing of the user.

The ventilation interface 150 may be relatively rigid and hard (as compared to the facial interface 152) and includes a gas entry port 22 to be connected to a gas feeder tube. The feeder tube is fluidically connected to a source of ventilation, such as a mechanical ventilator or CPAP machine. It is noted that the large central, circular entry port 156 does not need to be shaped, sized, or located as shown. Alternatively, a port 156 can be located on either or both sides of a center of the ventilation interface 150 or on the bottom of the ventilation interface 150.

Headgear may be attached to any part of the hybrid mask 148, including the ventilation, mouth, or nasal interfaces 150, 152, 154. The hybrid mask 148 is pressed against the face of the user in an attempt to provide a gas-tight seal. The headgear may be adjustable and may wrap entirely around the user's head to help toward the goal of a gas-tight seal between the user's face and the facial interface 152 of the hybrid mask 148.

The ventilation interface 150 is configured with at least one exhalation port 158. The exhalation port 158 can take any shape or have any size and can be in any number. For example, the port 158 can be located anywhere on the ventilation interface 150 or the facial interface 152.

The ventilation interface 150 is connected to the facial interface 152 in a removable but secure and gas-tight manner. The two interfaces 150, 152 can have any kind of securing connection—they can even be fixedly connected to one another if desired. The two interfaces 150, 152 may be integrally connected such that the two interfaces 150, 152 are one-piece.

The facial interface 152 includes a chin portion 160, an upper surface 162 defining a nasal interface connection 164, and a face-contacting periphery 166. The facial interface 152 is relatively soft compared to the ventilation interface 150 and, therefore, cushions the connection between the user's face and the relatively harder ventilation interface 150. The facial interface 152 is made of a material that feels soft to a user, for example, silicone or another elastomer having a durometer between 20 and 80. If desired, the chin portion 52 is shaped to extend around and include at least a part or the entirety of the chin of a user. The perimeter or face contacting periphery 166 of the facial interface 152 may be triangular, for example, or it may take on any regular or irregular geometric shape. The facial interface 152, including the face contacting periphery 166, can be manufactured in various anatomical mouth, nose, lip, cheek and chin geometries to accommodate different facial shapes and, thereby, provide proper and customized sealing for users.

The upper surface 162 of the facial interface 152 defines a nasal interface connection area for receiving the nasal interface 154 in a removable or integral manner.

The face-contacting periphery 166 may have a double-wall configuration to assist in reaching the goal of a substantially gas-tight seal to the user's face.

The nasal interface 154 is attached to the upper surface 162 of the facial interface 152 so that it can be configured to accommodate a user's nostrils in the most comfortable manner. The nasal interface 154 is attached, like a nipple to a bottle, to the upper surface 162 of the cushioning facial interface 152. In other words, the soft nasal interface 154 is squeezed and inserted into the upper surface 162 with a form-fitting connection that holds the nasal interface 154 securely, but removably, to the upper surface 162. This form-fitting or form-locking connection is one that connects two elements together due to the shape of the elements themselves. However, the connection may be, if desired, a force-locking connection, which locks the elements together by force external to the elements.

The nasal interface 154 has two separate nasal pillows 168 that can be connected to one another by a connecting bar 170 so that insertion of the pillows 168 can occur without one pillow 168 falling from the user's grasp while the other is being inserted into the facial interface 152. The connecting bar 170 also provides the user with the ability to insert the nasal pillows 168 into the facial interface 152 in a proper orientation. If desired, the nasal pillows 168 can be entirely separate from one another and, in such a configuration, are inserted separately and independently into the upper surface 162.

In the two nasal pillow configuration, the nasal interface connection 164 can be two portals 164.

Connection of each nasal pillow or conduit 168 to the portals 164 occurs, in the preferred embodiment, by forming the bottom end 172 of each nasal pillow with a first connecting surface and by forming the interior surface 174 of each of the portals 164 with a second connecting surface such that when the two contacting surfaces are positioned together, a gas-tight, removable connection occurs. In particular, the bottom end 172 of each pillow 168 is formed with rings defining at least one groove therebetween, the at least one groove having a given width. Correspondingly, the interior surface 174 of the portals 36 is formed with a thickness that is no greater than the given width. As such, when the nasal pillows 168 are compressed and placed inside the portals 164, the interior surface 174 mates with the rings and sits in the groove to form the substantially gas-tight connection.

The nasal interface 154 can be connected to the portals 164 or to the upper surface 162 of the facial interface 152 in any number of ways. For example, the elastic nasal interface 154 can be secured to the upper surface 162 with a locking mechanism such as a cotter pin, an elastic band, or a C-shaped spring clip. Alternatively, the nasal inserts 154 may be stretched to fit over small protrusions extending upwards from the upper surface 162. In yet another embodiment, the nasal pillows 168 may have threads that screw into corresponding threads in the upper surface 162. Other measures for connecting the nasal pillows 168 or nasal interface 154 to the facial interface 152 include, for example, forcing the nasal pillows 168 into a recess of the upper surface 162 or applying an adhesive or hook and loop type fasteners.

The two nasal pillows 168 can be integral with the facial interface 152. Interfaces 150, 152 and 154 can be integral with each other to be one-piece.

The pair of nasal pillows 168 can be replaced with a nasal triangle, where a nasal triangle is a mask unit that entirely surrounds the user's nose and seals against the upper lip, cheeks, and nose bridge of the user.

The nasal interface 154 may be removable and, therefore, disposable. The removable nasal interface 154 may be configured similar to the nasal inserts disclosed in the following patents, which are hereby incorporated by reference in their entireties: a) the Wood U.S. Pat. No. 6,807,967 issued Oct. 26, 2004 and entitled Ventilation Interface For Sleep Apnea Therapy, b) the Wood U.S. Pat. No. 6,776,162 issued Aug. 17, 2004 and entitled Ventilation Interface For Sleep Apnea Therapy, and c) the Wood U.S. Pat. No. 6,595,215 issued Jul. 22, 2003 and entitled Ventilation Interface For Sleep Apnea Therapy.

Another alternative embodiment can have the ventilation interface 150 where the facial interface 152 can be a single integral part and the nasal interface 154 can be a separate part. The nasal interface 154 can also be integral with the two other interfaces 150, 152 to form a one-piece mask having nasal pillows on the upper surface thereof. Any two of these three parts can be integral and then attached with the third part (i.e., 150 and 152 being integral, 152 and 154 being integral, or 150 and 154 being integral).

The ventilation interface 150 includes a first chamber 176 defined therein and the facial interface 152 includes a second chamber 178 defined by a gas exit 180 of the facial interface 152. When connected together to form the hybrid mask 148, the ventilation interface 150 and the facial interface 152 are shaped to provide an air reservoir in and around the mouth of the user. Accordingly, the rear-most edge (face-contacting periphery 166) of the facial interface 152 forms the only contact point between a) the two components 150 (ventilation interface) and 152 (facial interface) and b) the face of the user. These two components (150, 152) along with the nasal interface 154 are sized and shaped to facilitate producing laminar flow between the feeder tube, the gas entry port 156, the air reservoir, the nasal interface 154, the ventilation interface 150, the facial interface 152 and/or the at least one exhalation port 158. The exhalation port 158 may be adjustable so that the user can set a given air pressure prescribed by a physician.

The facial cream sealant 14 is applied to one or more of a) the face and b) the face contacting periphery 166. If the facial cream sealant 14 is applied to the face, the facial cream sealant 14 may be applied between the nose and the upper lips and around the rest of the mouth. The facial cream sealant 14 may also be applied to the inside of the nostrils or about the outside of the opening of the nostrils. The facial cream sealant 14 may also be applied about the upper end of the nasal pillows 168 where speckling is shown. The phantom line in FIG. 6C shows that the facial cream sealant may be spread about a greater area than the area defined by the face contacting periphery.

Figure 7:
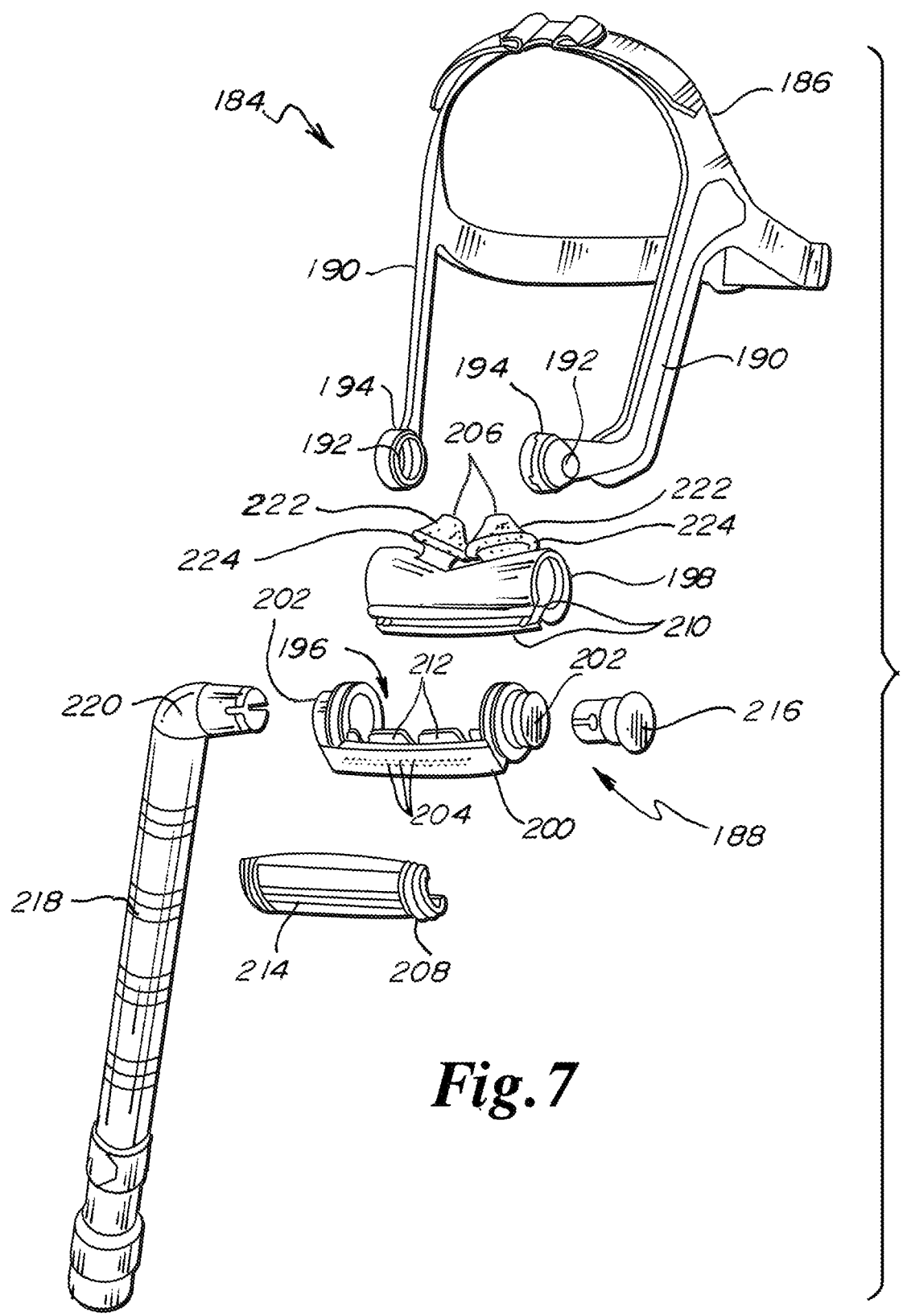
FIG. 7 is a perspective exploded view of a nasal pillow interface device.

FIG. 7 is a perspective exploded view of a nasal pillow interface device 184. As to CPAP nasal pillow device 184, the Ho et al. U.S. Pat. No. 9,084,863 issued Jul. 21, 2015 and entitled Respiratory Patient Interfaces is hereby incorporated by reference in its entirety.

The patient interface device 184 includes a headgear 186 and a nasal pillow assembly 188. The headgear 186 includes rigid or semi-rigid yokes 190 which provide stability to the sides of the headgear 186. In addition, the headgear 186 includes a headgear ring 192 having a seal ring 194 therein provided at the end of each yoke 190 for connecting the headgear 186 to the nasal pillow assembly 188 as described below.

The nasal pillow assembly 188 includes a frame 196 made of a rigid material such as, without limitation, a plastic material, which supports a pillow sleeve 198 made of a flexible material such as, without limitation, silicone. The frame 196 includes a flange portion 200 and connector portions 202 provided at each end of the frame 196. The flange portion 200 includes vent holes 204 through which exhaled gasses may pass. The pillow sleeve 198 includes nasal prongs 206 structured to be partial received within the nares or nostrils of the patient. Finally, the nasal pillow assembly 188 includes a clip 208 made of a rigid material such as, without limitation, a plastic material, the function of which is described below.

The patient interface device 184 is assembled by first assembling the nasal pillow assembly 188 by wrapping the pillow sleeve 198 around the frame 196 in a manner such that each of the lipped ends 210 of the pillow sleeve 198 is received in a space formed between respective retaining flanges 212 and the flange 200. Then, the clip 208 is slid over the flange 200 and the lipped ends 210. The clip 208 includes a rectangular opening 214 which leaves the vent holes 204 exposed when the nasal pillow assembly 188 is assembled. Next, the headgear 186 is connected to the nasal pillow assembly 188 by inserting each of the connector portions 202 of the frame 196 through a respective one of the headgear rings 192 and seals rings 194. Then, a cap 216 is inserted into one of the connector portions 202 and a tube assembly 218 having an elbow 220 is inserted into the other of the connector portions 202. The positions of the tube assembly 218 and the plug or cap 216 may be interchanged according to preference, e.g., the typical sleeping position of the patient. The tube assembly 218 is provided with a source of pressurized gas such as a CPAP machine.

The facial cream sealant 14 may be applied to the inside of the nostrils or about the outside of the opening of the nostrils. The facial cream sealant 14 may also be applied about the upper ends 222 of the nasal pillows or prongs 206 where speckling is shown. The facial cream sealant 14 may also be applied to the annular base 224 of the tapering prong 206.

Figure 8A:
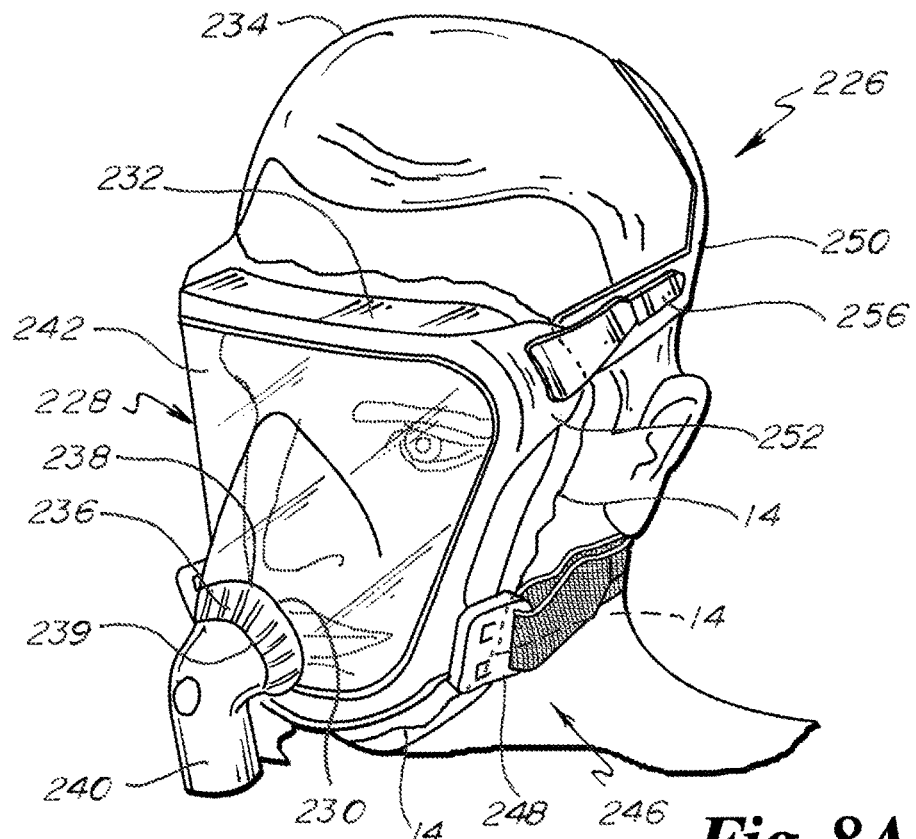
FIG. 8A is a side elevation view of a total face mask assembly.
Figure 8B:
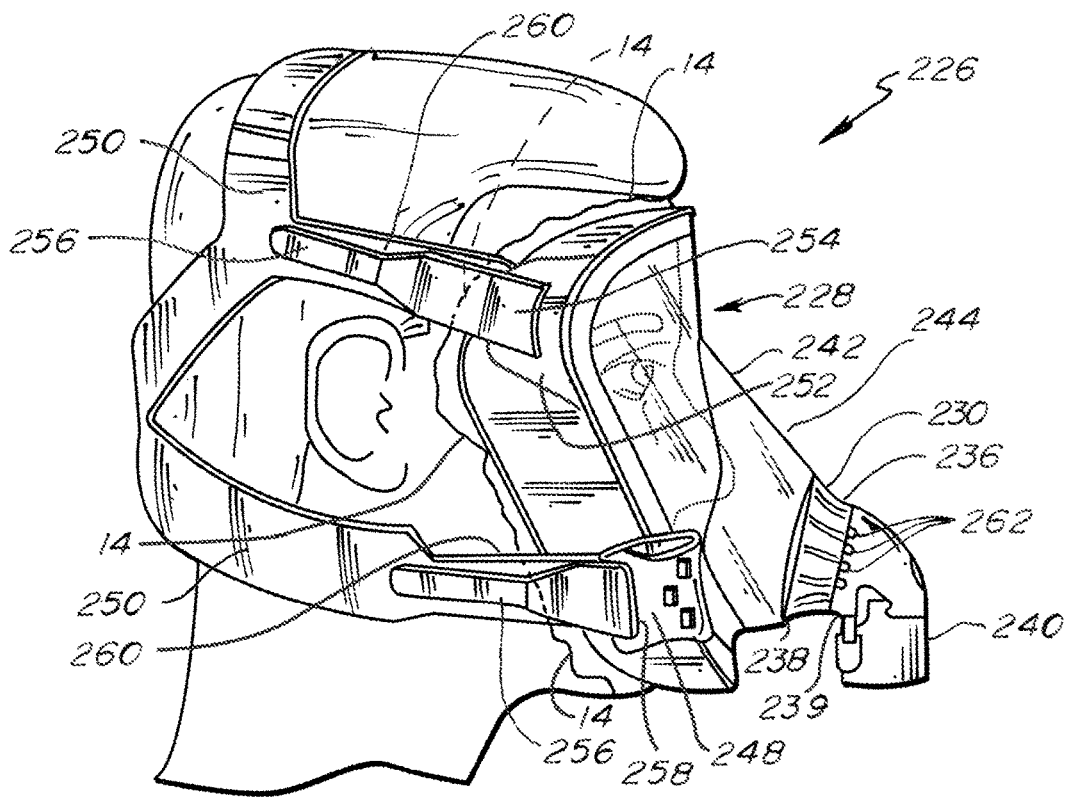
FIG. 8B is a perspective view of the total face mask assembly of FIG. 8A.

FIGS. 8A and 8B show a total face mask assembly 226 for use in a therapeutic gas delivery. As to the total face mask assembly 226, the Todd et al. U.S. Pat. No. 8,573,217 issued Nov. 5, 2013 and entitled Face Mask is hereby incorporated by reference in its entirety.

The total face mask assembly 226 may generally include a mask body 228 having an opening 230 for reception of gas. The total face mask body 228 includes a seal structure 232 for sealingly engaging with the face of the patient 234 in surrounding relation to at least the nose and mouth (and optionally the eyes) of the patient 234. The total face mask assembly 226 includes a breathing circuit interface 236 for connecting the mask body 228 with a pressurized breathing gas supply. As disclosed in more detail later, the breathing circuit interface 236 has a first portion 238 rotatably connected with the mask body 228 and a second portion 239 constructed and arranged to connect with a conduit 240 for delivering the gas to the patient 234 through the opening 230.

The breathing circuit interface 236 and the conduit 240 connects the mask body 228, via a circuit tubing, to a source of gas, e.g., a blower, a CPAP machine, a ventilator or other suitable device, for providing breathing gas to the patient 234. The second portion 239 of the breathing circuit interface 236 is releasably connected with the conduit 240 to enable different types of conduits 240 to be connected to the mask body 228. In addition, a rotatable or swivel connection between the breathing circuit interface 236 at the first portion 238 thereof with the mask body 228 allows the elbow shaped conduit 240 to rotate after connection to enable the conduit 240 to extend in any direction within 360 degrees of rotation for connecting with the tubing. It should be appreciated that for some purposes the breathing circuit interface 236 may also be considered to be part of the mask body 228.

The mask body 228 includes a rigid portion 242, formed from a clear plastic material, and the aforementioned flexible peripheral seal structure 232. The flexible peripheral seal structure 232 is attached around the rigid portion 242 of the mask body 228. A protrusion 244 extends forwardly from a forward central portion of the rigid portion 242 of the mask body 228 and is shaped to accommodate the nose and the mouth of the patient 234. The protrusion 244 is generally pear shape about its periphery, where it meets the flatter parts of the rigid portion 242 and includes the opening 230 located in the forwardmost portion thereof. The protrusion 244 includes a pair of indentations located horizontally on either side of the opening 230. The pair of indentations serves as finger receiving indentations and provides a region for an individual to grip the mask body 228 when placing and removing the mask body 228 on the patient's face.

The mask body 228 is adapted to be connected with headgear assembly 246 that can be used to mount the mask body 228 on the head of the patient 234. A pair of headgear attachment clips 248 provides for interface and connection with lower headgear mounting strap portions 250 of the headgear assembly 246. A pair of headgear attachment members is provided for connectably receiving the headgear attachment clips 248, and a pair of spaced upper headgear strap retaining tabs 252, each having an elongated opening 254 therethrough, is provided for receiving upper headgear mounting strap portions 250 of the headgear assembly 246. The pair of headgear retaining tabs 252 is disposed on the opposite upper sides of the rigid portion 242 of the mask body 228. The pair of headgear attachment members is disposed on opposite, lower sides of the rigid portion 242 of the mask body 228. Each headgear retaining tab 252 is integrally formed with rigid portion 242 and extends outwardly from the flexible peripheral seal structure 232.

The headgear assembly 246 that is used to mount the mask body 228 to the head of a patient 234 takes the form of straps. An end portion 256 of each of the two headgear straps 250 (only one shown in FIG. 8B) is threaded through the elongated opening 254 of the headgear retaining tab 252, and the end portion 256 of the lower headgear straps 250 are threaded through the elongated opening 258 of the headgear attachment clip 248. The end portions 256 include hook material and is bent back into engagement with the adjoining surface 260, formed of loop material, on the straps 250 so as to form a hook and loop (or VELCRO®) type connection. There are other ways for securing the end portion of the headgear strap to itself or to the headgear attachment clip 248 and/or to the headgear attachment tab 252, such as snap connections, buckles, or locking clamps. The headgear 246 is adjustable, as the straps 250 can be pulled further through the opening 254 of the headgear retaining tab 252 or the elongated opening 258 of the headgear attachment clip 248 to accommodate smaller diameter head sizes.

Total face mask assembly 226 includes exhalation ports or grooves 262 between the breathing circuit interface 236 and conduit 240.

The facial cream sealant 14 is applied to at least the endless or continuous peripheral seal structure 232 which endlessly surrounds the mouth, face and eyes of person 234 using a CPAP machine. That is, the facial cream sealant 14 is applied about the endless peripheral seal structure 232 and, optionally, outwardly of the seal structure, such as shown in FIGS. 8A and 8B, such that an endless facial cream seal 14 is formed. FIGS. 8A and 8B show that the facial cream sealant 14 may be spread beyond an area on the face defined by the endless peripheral seal structure 232. Patients may self adjust the total face mask assembly 226 such that the facial cream sealant 14 may be spread over an area larger than that defined by the endless peripheral seal structure 232 prior to placing the total face mask body 228 on the face.

Figure 9A:
FIG. 9A is an elevation view of a respirator showing the present sealant in phantom and in endless form about the periphery of the respirator.

An active face mask or respirator or gas mask 264 is shown in FIG. 9A. As to mask 264, the Matich U.S. Pat. No. 7,017,577 issued Mar. 28, 2006 and entitled Face Mask With Seal And Neutralizer is hereby incorporated by reference in its entirety.

Mask 264 has a pair of one way valves 266 for air intake. Another valve 268 is a one way exhalation port for the exhalation of air. Mask 264 further includes a covering 270 having a rubber or elastomeric periphery 272 for being pressed against a face. The rubber or elastomeric periphery 272 may be spread with the facial cream sealant 14 of the present invention. The facial cream sealant 14 is shown in phantom in FIG. 9 where such sealant 14 is not spread beyond a periphery defined by the periphery 272. Such sealant 14 is also shown in solid lines in FIG. 9A where such facial cream sealant has been spread beyond the periphery 272. A positive air pressure exists within active face mask 264 of about three to four pounds. The conventional purpose of the positive pressure is to guard against the flow of smoke or other fluid or substance into the mask, whether such an inward flow would be about the periphery 272 or through a leak somewhere in the mask 264. With the facial cream sealant 14 of the present invention, air (such as in a tank on the back of the user) is conserved. That is, less air is lost flowing out of the mask 264 via the periphery 272. However, there is still a positive pressure within the mask 264 to force air through any leaks in the sealed periphery 272 or any leaks elsewhere. Face mask 264 extends only around the nose and the mouth.

Figure 9B:
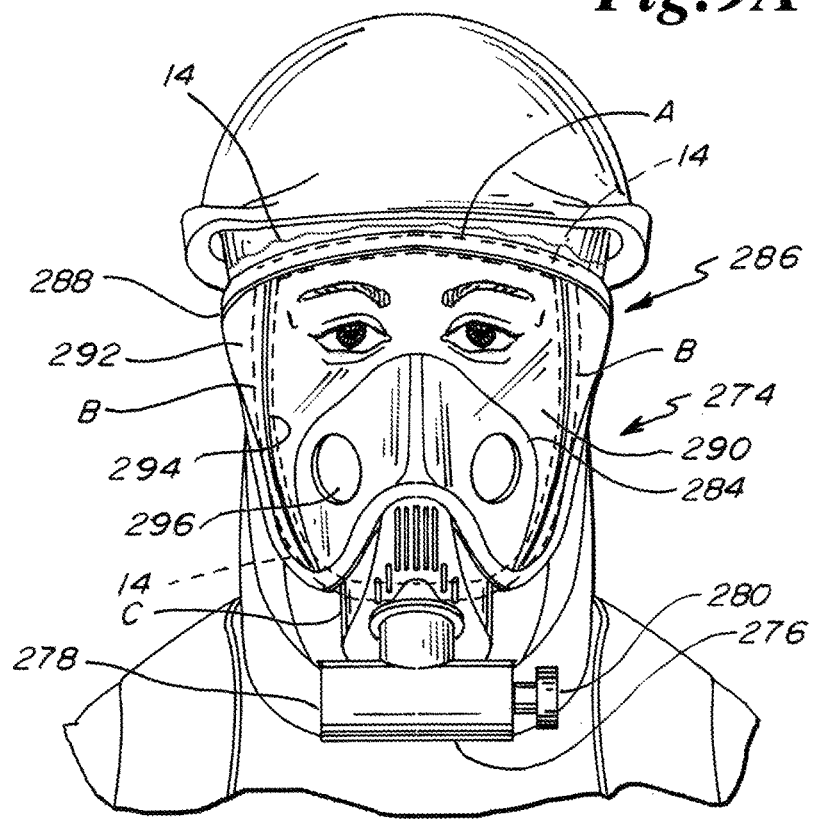
FIG. 9B is an elevation view of a respirator showing the present sealant in phantom and in endless form about the periphery of the respirator.

An active face mask or respirator or gas mask 274 is shown in FIG. 9B. As to mask 274, the Matich U.S. Pat. No. 7,017,577 issued Mar. 28, 2006 and entitled Face Mask With Seal And Neutralizer is hereby incorporated by reference in its entirety.

Active face mask 274 includes an air intake T-connection 276 having an air intake coupler end 278 and an air intake valve 280. The T-connection 278 is engaged to an air exhaust piece 282 and is further engaged to a nose and mouth piece 284 that confronts the mouth and nose. The combination of the air exhaust piece 282 and nose and mouth piece 284 is a base unit that includes a valve arrangement that permits fresh air into the nose and mouth piece 284 via the T-connection 276 and permits exhaled air out of the nose and mouth piece 284 and out of the mask 274 via the air exhaust piece 282. A face shield 286 is engaged to the base unit of the air exhaust piece 282 and nose and mouth piece 284 via a base hard plastic strip 288. The relatively rigid base strip 288 runs about the periphery of the face shield 286. The base strip 288 forms the shape of an inverted U between the nose and mouth piece 284 and the air exhaust piece 282. The base strip 288 runs upwardly from the inverted U shape to be disposed along the each of the sides of the face to a position near the ears so as to form a W shape. Then the base strip 288 runs inwardly from the ears and across the forehead. A clear plastic shield 290 is engaged to the outer face of the base strip 288. The face shield 286 further includes a rubber or elastomeric piece 292 (a resilient piece 292) that is engaged to the inner face of the base strip 288 except for the inverted U-shaped portion of the base strip 288, where the resilient piece 292 is engaged to an underside of the unit having the exhaust 282 and the mouth and nose piece 284 and where the resilient piece 292 cradles the chin. The resilient piece 292 thereby extends completely about the eyes, mouth and nose as a whole. The resilient piece 292 is relatively wide at the sides of the face. The resilient piece 292 includes an eye, nose and mouth opening defined by an inner edge 294 that completely surrounds the eyes, nose and mouth. The air exhaust piece 282 is generally external to the clear plastic shield 290 and the nose and mouth piece 284 is internal to the clear plastic shield 290. The nose and mouth piece 284 includes vents 296 from which air flows to the inner face of the clear plastic shield 290 to minimize formation of a condensate or fog on the inner face of the clear plastic shield 290. The facial cream sealant 14 of the present invention is spread upon the active face mask 274 between the face and the resilient piece 292 as shown in phantom lines in FIG. 9B. The facial cream sealant 14 is engaged at a position A (between the face and the portion of the resilient piece 292 that is engaged under a portion of the base strip 288 that runs across at least a part of the forehead), at two positions B (between the face and the inner edge 294 of each of the right side and left side portions of the resilient piece 292), and at a position C (between the face and the portion of the resilient piece 292 that cradles the chin). The facial cream sealant 14 runs continuously from position A to position B to position C to position B to position A to run continuously or endlessly about the eyes, nose and mouth as a whole. As with the active face mask of FIG. 9A, face mask 274 permits air to be conserved by the user (such as a fireman or diver). Conventionally, air is slowly lost about portions of the strip 288 and resilient piece 292 because of the positive air pressure of about three or four pounds inside of the mask 274. Conventionally, this loss of air is intended to guard against an inflow of smoke or other fluid. With the facial cream sealant 14, the positive air pressure is maintained to guard against inflow yet less fresh air from a tank is required, thereby providing the fireman or firewoman more time inside a smoke filled environment. As shown in solid lines in FIG. 9B, the facial cream sealant 14 may also be spread beyond the endless periphery defined by resilient piece 292.

Figure 10A:
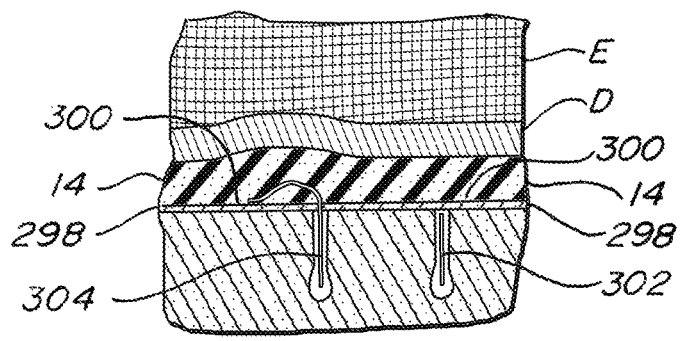
FIG. 10A is a cross-section of the present sealant between a periphery of a face mask and the skin of a human face.

The epidermis is the topmost layer of the skin and is shown in FIG. 10A as reference numeral 298. The stratum corneum (or horny layer) is the outermost layer of the epidermis and consists of mainly dead keratinocytes, hardened proteins (keratins) and lipids, all of which combine to form a protective crust. Dead epithelial cells of the stratum corneum are continuously flaked off. The skin friendly facial cream sealant 14 of the present invention preferably minimizes separation of the stratum corneum from the face.

The facial cream sealant 14 is not a skin unfriendly adhesive, where, upon a peeling off of the skin unfriendly adhesive by hand, such peeling off separates the stratum corneum from the next immediate layer of the epidermis.

It should be noted that some definitions of the epidermis do not include the stratum corneum as part of the epidermis. In such a case, a skin unfriendly adhesive is such that, upon a peeling off of the skin unfriendly adhesive by hand, such a peeling off separates the stratum corneum from the epidermis or maximizes the separation of the stratum corneum from the epidermis. With such a definition of the epidermis, the facial cream sealant 14 is not sufficiently aggressive to penetrate the stratum corneum and bond to the epidermis.

The facial cream sealant 14 is skin-friendly. As to a skin friendly substance, the Fujisawa et al. U.S. Pat. No. 6,262,330 issued Jul. 17, 2001 is hereby incorporated by reference in its entirety. In the Fujisawa et al. U.S. Pat. No. 6,262,330, a skin friendly substance has an adhesive strength to bakelite of at most (1.5 N)/(15 mm). Further as to a skin-friendly substance, the Kitazaki et al. U.S. Pat. No. 6,297,421 issued Oct. 2, 2001 is hereby incorporated by reference in its entirety. In the Kitazaki et al. U.S. Pat. No. 6,297,421, its skin-friendly substance has a strength of 0.6 to 10.0 N/24 mm in terms of the adhesive strength of a pressure sensitive tape 24 mm in width to a bakelite panel as measured in accordance with the 180 degree peeling method described in JIS Z 0237. The Kitazaki et al. U.S. Pat. No. 6,297,421 teaches that if the adhesive strength to the bakelite panel is too low, the adhesive strength is insufficient for human skin and if the adhesive strength to the bakelite panel is too high, disadvantages such as separation of the horny layer are easy to occur. It should be noted that the present sealant 14 is not a tape.

The facial cream sealant 14 does not involve the separation of the horny layer. A facial cream sealant 14 causes no or minimal pain when peeled off the skin. A facial cream sealant 14 minimizes the separation of corneocytes or the corneum upon peeling. The facial cream sealant 14 minimizes the separation of the horny layer. When the facial cream sealant 14 is peeled off the skin or washed off the skin or rubbed into the skin, little or none of the horny layer is peeled off.

The facial cream sealant 14 is not a skin unfriendly substance, where a skin unfriendly substance a) bonds to the horny layer skin, b) bonds below the horny layer such as to the epidermis or to living cells of the epidermis (where the horny layer may be defined as dead cells of the epidermis), c) has an adhesive strength to bakelite of more than (1.5 N)/(15 mm), and d) has an adhesive strength of more than (1.5 N)/(15 mm) to about (20 N)/(15 mm). As to the measurement of these ranges, the Fujisawa et al. U.S. Pat. No. 6,262,330 issued Jul. 17, 2001 and Kitazaki et al. U.S. Pat. No. 6,297,421 issued Oct. 2, 2001 are hereby incorporated by reference in their entireties.

FIG. 10A further shows the surface 300 of a human face, the first layer of skin 298, and a hair 302 that has been cut or dissolved to a level below the surface 300 of the human face. FIG. 10A further shows a hair 304 that has not been cut or dissolved or removed such that hair 304 extends to an outside of the skin surface 300. The facial cream sealant 14 is sufficiently receptive to hair 304 so as to receive the hair therein.

FIG. 10A further shows parts D and E. Parts D and E represent any parts of any of the masks of the present invention, such as the endless peripheral portions of the masks that surround one or more of the mouth, nose, and eyes.

Figure 10B:
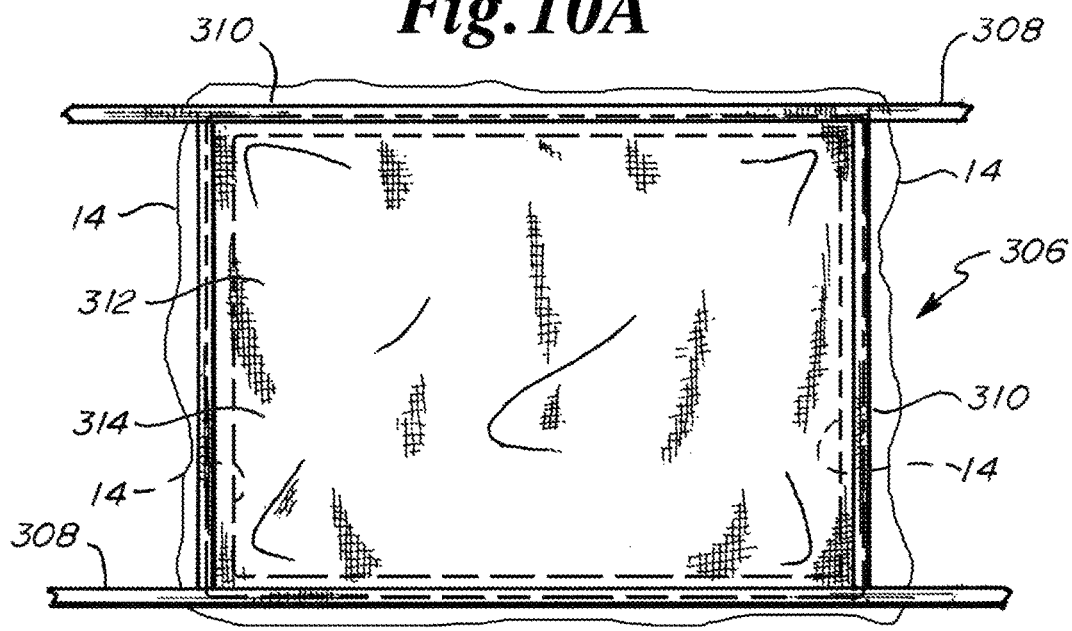
FIG. 10B is a top view of a face mask showing the present sealant in phantom and in endless form about the periphery of the face mask.

FIG. 10B shows a planar mask 306. As to planar mask 306, the Matich U.S. Pat. No. 8,381,727 issued Feb. 26, 2013 and entitled Face Mask With Seal Within Seal And Optional Bridging Seal is hereby incorporated by reference in its entirety.

Planar mask 306 is disposed in generally a plane prior to being applied to a face, such as over only the mouth or over only the nose or over only the mouth and nose. Mask 306 is rectangular in shape and includes one pair of two opposing parallel edges and another pair of opposing parallel edges. Mask 306 may be referred to as a surgical mask. Mask 306 may include bands 308 that are rubber or elastomeric. Bands 308, where such engage the rectangular periphery 310 of mask 10D, are parallel. Mask 306 includes a covering 312. Covering 312 is a filter. Covering 312 permits air to pass into and out of the covering 312 but prevents minute particles of a given size from passing into or out of the covering 312. Covering or filter 310 is structured to permit air into and out of the covering 310. Covering or filter 310 is structured to minimize a flow of substances or particles into and out of the covering 310. Covering 312 is flexible.

The facial cream sealant 14 is engaged to the inside 314 of mask 306 about the endless periphery 310 of the mask 306. The peripheral facial cream sealant 14 is shown by phantom lines. As shown by solid lines, the facial cream sealant 14 can also extend beyond the endless periphery 310 so as to cover a greater surface area on the skin of the face than that bounded by the endless periphery 310.

Figure 10C:
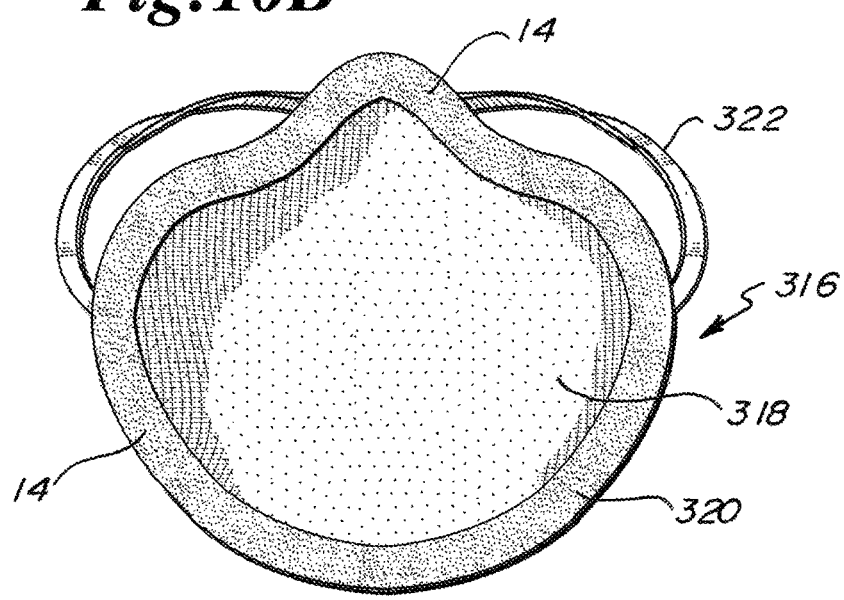
FIG. 10C is a rear view of a face mask showing the present sealant in speckling and in endless form about the periphery of the face mask.

FIG. 10C shows a convex face mask 316. As to mask 316, the Matich U.S. Pat. No. 7,017,577 issued Mar. 28, 2006 and entitled Face Mask With Seal And Neutralizer is hereby incorporated by reference in its entirety.

Convex mask 316 for only the nose and mouth includes a convex covering 318. The convex covering 318 of face mask 316 is a filter that permits air to pass through but which traps particulates. The particulates may be smoke particulates or anthrax or other relatively small substances.

The covering 318 includes a portion that projects outwardly of the mouth and nose. This portion is within an endless periphery 320 and is convex relative to an exterior of the covering 318. With such a convex portion, the covering 318 is spaced from the mouth and away from spit and saliva that may degrade the mask 316. Further, spit and saliva is a fluid that may permeate or move through the covering 318, dissolve the toxin, and then move back through the covering 318, drawing the toxin with it. Further, spit and saliva may reduce the potential of any neutralizing agent in the covering 318 to neutralize a toxin as the spit and saliva may dilute the neutralizing agent or block the activated portions of the neutralizing agent from gaining access to the toxin. The facial cream sealant 14 is shown by speckling on the endless band or periphery 320. The facial cream sealant 14 may be spread not only on the periphery 320 but beyond the periphery 320 to cover a larger portion of the face. Such a spreading may also involve portions of the face that are originally inside of an area defined by periphery 320, and such an inside spread is applicable to all of the other masks disclosed herein. Mask 316 includes an elastomeric band 322 having two ends engaged to the mask 316. Elastomeric band 322 surrounds the rear of a head of a user to keep the mask 316 in place over the nose and the mouth.

Figure 11A:
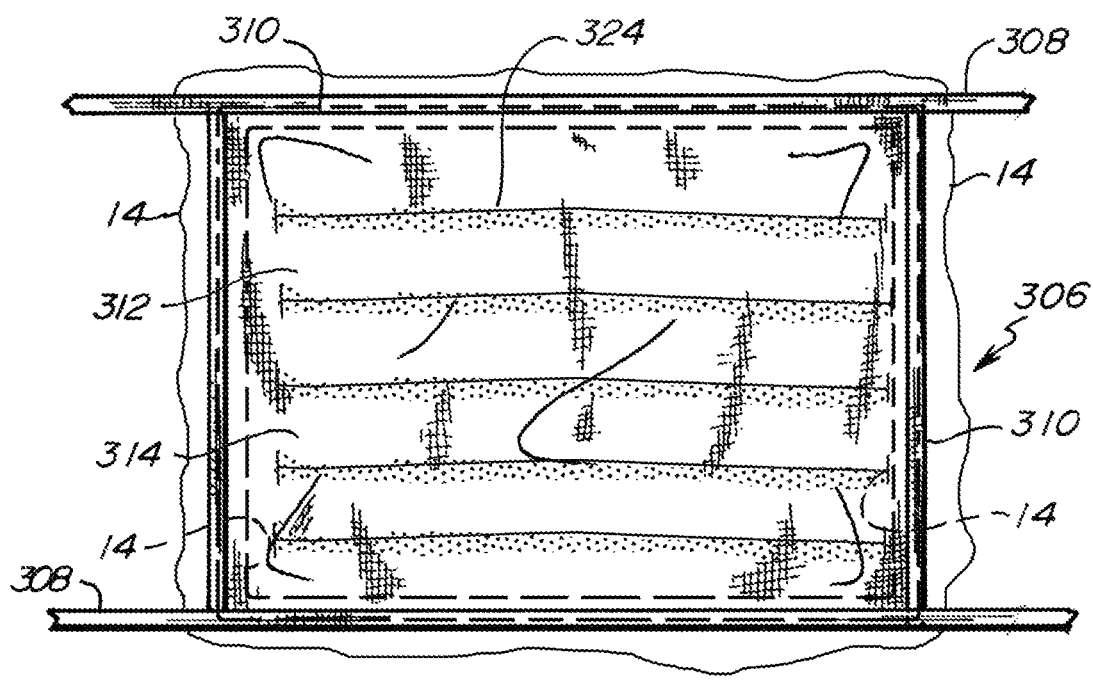
FIG. 11A is a top view of a pleated face mask showing the present sealant in phantom and in endless form about the periphery of the face mask.

FIG. 11A shows the planar mask 306 of FIG. 10B but with pleating 324. The pleating 324 permits the mask 306 to expand, such as in height or in length or both in height and length. The pleating or double folds are present in and are part of the covering 312 of the mask 306 of FIG. 11A. The covering 312 itself forms the pleats 324 or double folds. The planar mask of FIG. 11A employs the facial cream sealant 14 in the same way as the planar mask of FIG. 10B.

Figure 11B:
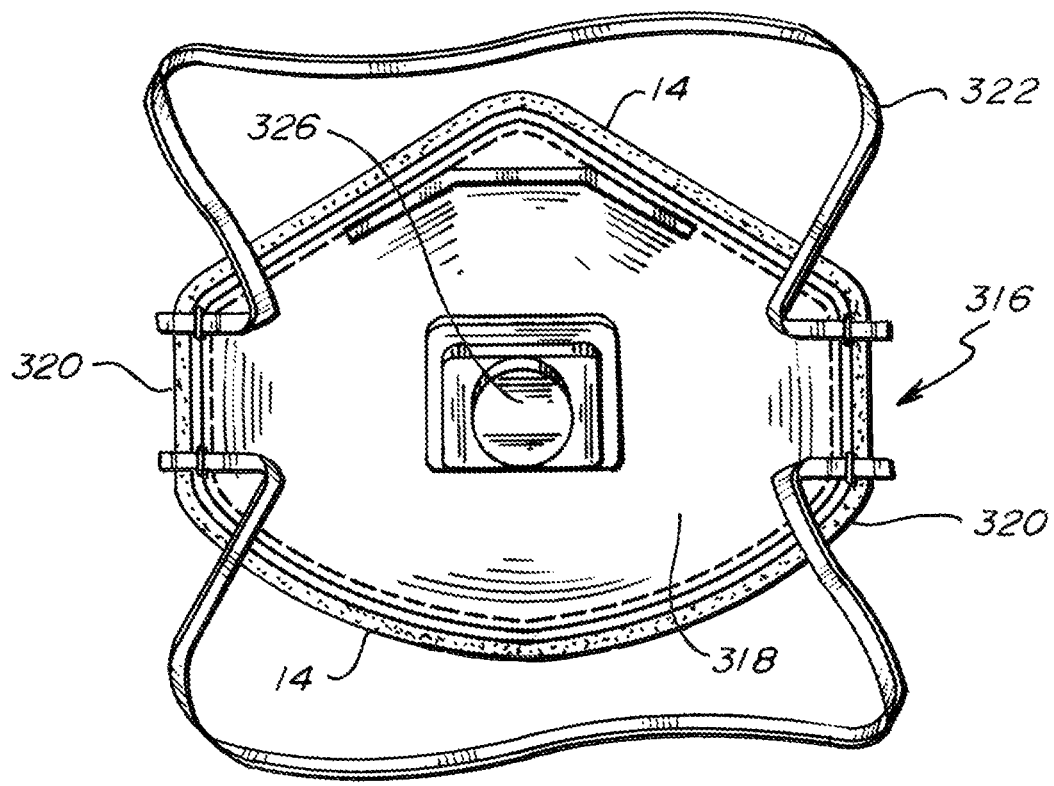
FIG. 11B is a bottom view of a face mask showing the present sealant in speckling and in endless form about the periphery of the face mask.

FIG. 11B shows the convex face mask 316 of FIG. 10C but with a one way valve 326 that permits exhalation of air but not the inhalation of air. Convex face mask 316 of FIG. 11B also has an endless peripheral band 320 of a different peripheral shape than mask 316 of FIG. 10C. Convex face mask 316 of FIG. 11B also has two elastomeric bands 322 instead of the single band 322 of the mask of FIG. 10C. The mask of FIG. 11B employs the facial cream sealant 14 in the same way as the mask of FIG. 10C.

The present sealant 14 may also be used on oxygen masks. As to an oxygen mask where the present sealant 14 may cover an annular endless band face confronting region of the oxygen mask, the Hu U.S. Pat. No. 9,272,108 issued Mar. 1, 2016 and entitled Oxygen Mask is hereby incorporated by reference in its entirety.

The present respirator or mask facial sealant 14 is a safe skin moisturizer sealant 14 that can be applied by the user out of a tube, anytime, anyplace on every type or model of respirator or mask.

The present facial sealant 14 seals between the face and respirator or mask to stop or reduce the inward or outward movement of unfiltered hazardous air that would otherwise leak between the face and respirator or mask.

The present facial sealant 14 forms a seal on faces with or without facial hair.

The present facial sealant 14 is safe to use because it is a skin moisturizer.

The present facial sealant 14 has the right amount of tackiness to seal between the face and respirator or mask.

When finished with use, the present facial sealant 14 is easy to clean up on face by being rubbed into skin as a skin moisturizer.

The present facial sealant 14 can be used on all types and models of respirators or masks. In other words, there are a great variety of respirators and masks that have certain peripheral structures. These certain peripheral structures are intended to fit a great variety of faces having unique noses, unique cheeks, unique cheekbones, unique mouths and unique chins. Such an intention is admirable. Such a goal is likely impossible to achieve. However, the present facial sealant 14 can fill in the peaks and valleys and openings that are likely to exist between the peripheral structure of a face mask and the unique structure of one's face. A perfect seal with the present facial sealant 14 is in fact obtainable with little or no effort.

The present facial sealant 14 can be used on all shapes and sizes of faces as a seal for respirators or masks.

The present facial sealant 14 can be put on at anytime, anyplace because it is in a tube and because it can be applied with the user's finger or by sliding the tube along the respirator or mask.

The present facial sealant 14 stops or reduces the movement of hazardous unfiltered air in or out between the face and the respirator or mask such that hazardous unfiltered air is unable to enter lungs.

Facial hair will not affect the present seal between the face and the respirator formed by the present sealant 14 because the sealant 14 surrounds the hair with a tacky surface, thereby matting the hairs together with each other and/or with the face and/or with the periphery of the respirator or mask, thereby forming a seal absolutely.

The present facial sealant 14 stays creamy but highly tacky throughout use at room temperature.

The present facial sealant 14 stays creamy but highly tacky throughout use at temperatures between about minus 20 degrees Fahrenheit and about 110 degrees Fahrenheit.

The main elements of my invention include a creamy but highly tacky skin moisturizer 14 or sealant 14 that stays creamy but highly tacky during the full time of use. The skin moisturizer 14 or sealant 14 is to be 1) dispensed from a tube by user, 2) applied by finger or by sliding a tube filled with the sealant 14 along the periphery of a respirator or mask, 3) applied to a face with or without facial hair, and/or 4) may be rubbed into the skin anywhere on the body, including the face, as a skin moisturizer 14 in a clean-up operation.

The present seal 14 saves lives.

The present seal 14 is a health facial sealant 14.

The present seal 14 can be used on all types of respirators and masks.

The present seal 14 saves lungs and thus saves lives.

The present seal 14 reduces the risks and hazards of unfiltered air entering lungs between the faces and the respirator or mask.

The present seal 14 reduces the risks for users with or without facial hair.

The present seal 14 is dermatologically safe.

The present seal 14 is an excellent skin moisturizer.

The present seal 14 may be scented or non-scented.

The present seal 14 minimizes or outright stops movement of the respirator or mask relative to the face and, at the same time, allows the CPAP mask to float without drifting sideways or up and down on the sealant 14. The sealant 14 allows the CPAP mask to be spaced from the skin of the face.

The present seal 14 and its unique formula protects against hazardous air from leaking between face and the respirator or mask.

Unsealed or nonsealed respirators and masks have been shown to have an inward leakage failure as high as 43% during use.

The present seal 14 is enriched with a mix of nutrients, which, as well as providing nutrients to the skin, moisturizes one or more layers of skin.

In use, the present health sealant 14 is applied generously to the respirator or mask and/or to the face at areas where the respirator or mask will make contact with the face.

With faces with facial hair, the present health sealant 14 is to be applied generously into the beard and/or the sealant 14 is rubbed in an endless band fashion at respirator or mask contact areas, thereby creating an air tight sealant protective fence 14 or barrier 14 or living barrier 14 or flexible barrier 14 between face and respirator or mask.

After use of the face mask or respirator, the face mask is removed from the face. Then, to clean the face, excess sealant 14 may be wiped off the face with a towel and/or the present sealant 14 may be rubbed into the skin as a moisturizer 14. In other words, the sealant 14 may be rubbed into the skin without employing a clean-up operation with a towel. Or a clean-up operation may be performed with a towel or at a sink with water and/or soap and water, whereupon any remaining sealant 14 may be simply rubbed into the skin.

The respirator or mask may be cleaned with a towel for a subsequent use or the respirator or mask may be disposed of if of the single use type.

The sealant or topical composition 14 includes one or more of the following components and preferably all of the following components:

a) water (component A);
b) a vegetable oil (component B)
c) a hydrophilic nonionic surfactant (component C)
d) a fatty alcohol emollient (component D)
e) a humectant (component E)
f) a sorbitan ester nonionic surfactant (component F)
g) a sheatree derivative (component G)
h) a linoleic acid component (component H)
i) a vitamin antioxidant component (component I)
j) a filler (component J)
k) a thickening agent (component K)
l) a metal chelator (component L)
m) a basic neutralizing agent (component M)
n) an antimicrobial/preservative agent (component N)

Each of the above components is set out in detail below, where "wt %" means percent by weight of the ingredient relative to the weight of the composition 14 or sealant 14 as a whole.

A. Water (Component A)

The present sealant 14 may include a solvent or emulsifier. The preferred solvent or emulsifier is water. Oil and water components of the present sealant 14 may make up the cream or lotion nature of the sealant 14. The water that is included is free of toxins, pollutants and microbes. Water used in the sealant 14 may be distilled water, purified water, or aqua. Purified water is preferred. Water is a diluent. Water may be a saline.

The water or diluent or saline may be present in the composition 14 in an amount between about 1 wt % and 99% wt %, particularly about 50 wt % to about 99 wt %, preferably about 55 wt % to about 95 wt %, more preferably about 60 wt % to about 90 wt %, even more preferably about 65 wt % to about 90 wt %, and still more preferably from about 65 wt % to about 85 wt %.

In some embodiments, the water or diluent or saline may be present in the composition 14 in an amount between about 70 wt % and about 99 wt % or in an amount between about 70 wt % and about 95 wt % or in an amount between about 70 wt % and about 90 wt % or in an amount between about 70 wt % and about 85 wt %.

In some embodiments, the water or diluent or saline may be present in the composition 14 in amount over about 70 wt %.

B. Vegetable Oil (Component B)

The present sealant 14 may include coconut oil or a coconut oil derivative or a component or ingredient made from coconut oil or coconut acid, such as hydrogenated coconut oil, hydrogenated coconut acid, coconut alcohol, butylene glycol cocoate, caprylic/capric/coco glycerides, cocoglycerides, coconut oil decyl esters, decyl cocoate, ethylhexyl cocoate, isodecyl cocoate, lauryl cocoate, methyl cocoate, octyldodecyl cocoate, pentaerythrityl cocoate, tridecyl cocoate, magnesium cocoate, potassium cocoate, sodium cocoate, ammonium cocomonoglyceride sulfate, sodium cocomonoglyceride sulfate, hydrogenated cocoglycerides, potassium hydrogenated cocoate and sodium hydrogenated cocoate.

The function or role of the coconut oil or coconut acid, a vegetable oil, or an ingredient made therefrom may be as: anticaking agents, emulsion stabilizers, beard or hair conditioning agents, opacifying agents, skin-conditioning agents (emollients), skin-conditioning agents (occlusive), slip modifiers, surfactants (cleansing agents), surfactants (emulsifying agents), surfactants (foam boosters), viscosity increasing agents (aqueous), viscosity increasing agents (nonaqueous).

A vegetable oil is a triglyceride extracted from a plant. Preferably, a suitable vegetable oil for the present invention refers to a plant oil that is liquid at room temperature. However, vegetable oils that are solid at room temperature may be used, and these vegetable oils may be referred to as vegetable fats or vegetable waxes. A vegetable oil may be referred to as a vegetable seed oil because, in commercial practice, oil is extracted primarily from seeds. A vegetable oil may be a liquefied triglyceride.

Suitable vegetable oils include but are not limited to soybean oil, corn oil, cottonseed oil, palm oil, peanut oil, canola (rapeseed) oil, safflower (carthamus) oil, sunflower seed oil, sesame seed oil, rice bran oil, coconut oil, canola oil, soya oil, linseed or flaxseed oil, avocado oil, olive oil, cocoa bean, illipe, sal nut, mango kernel fat and their derivatives and mixtures thereof. Component B may include PGPR (polyglycerol polyricinoleate, a castor bean derivative).

The vegetable oil may be an edible grade vegetable oil.

A purified vegetable oil is preferred. A purified and deodorized vegetable oil is even more preferred. As to purified and deodorized vegetable oils, the Copeland et al. U.S. Pat. No. 6,172,247 B1 issued Jan. 9, 2001 and entitled Methods For Refining Vegetable Oils And Byproducts Thereof is hereby incorporated by reference in its entirety.

Component B may be referred to as a first vegetable oil component or first vegetable oil component mixture.

Component B may be an emollient, skin softener and skin protectant.

Component B may be present in the composition 14 in amount between about 1.0 wt % to about 25.0 wt %, preferably about 2.0 wt % to about 25.0 wt %, more preferably about 3.0 wt % to about 25 wt %, even more preferably about 4.0 wt % to about 25 wt %, and still more preferably from about 5.0 wt % to about 25 wt %.

In some embodiments, component B may be present in the composition 14 in an amount between about 5.0 wt % and about 20.0 wt % or in an amount between about 7.0 wt % and about 20.0 wt % or in an amount between about 10.0 wt % and about 20.0 wt % or in an amount between about 13.0 wt % and about 20.0 wt %.

In some embodiments, component B may be present in the composition in an amount less than 20 wt %.

Coconut oil, or a coconut oil derivative, may be present in the composition 14 in amount between about 1.0 wt % to about 25.0 wt %, preferably about 2.0 wt % to about 25.0 wt %, more preferably about 3.0 wt % to about 25 wt %, even more preferably about 4.0 wt % to about 25 wt %, and still more preferably from about 5.0 wt % to about 25 wt %.

In some embodiments, coconut oil, or a coconut oil derivative, may be present in the composition 14 in an amount between about 5.0 wt % and about 20.0 wt % or in an amount between about 7.0 wt % and about 20.0 wt % or in an amount between about 10.0 wt % and about 20.0 wt % or in an amount between about 13.0 wt % and about 20.0 wt %.

In some embodiments, coconut oil, or a coconut oil derivative, may be present in the composition in an amount less than 20 wt %.

C. A Hydrophilic, Nonionic Surfactant or Hydrophilic, Nonionic Solubilizing Agent (Component C)

The present sealant 14 may include a first surfactant, specifically a hydrophilic, nonionic surfactant or a hydrophilic, nonionic solubilizing agent. A hydrophilic nonionic surfactant or hydrophilic, nonionic solubilizing agent helps other ingredients to dissolve in a solvent in which they would not normally dissolve. A hydrophilic nonionic surfactant or hydrophilic, nonionic solubilizing agent also helps to form emulsions by reducing the surface tension of the substances to be emulsified. One preferred hydrophilic nonionic surfactant or hydrophilic, nonionic solubilizing agent is a polysorbate. Preferred polysorbates or polysorbate surfactant agents or polysorbate solubilizing agents or include, but are not limited to, Polysorbate 20 (polyoxyethylen-(20)-sorbitanmonolaurate), Polysorbate 21 (polyoxyethylen-(4)-sorbitanmonolaurate), Polysorbate 25, Polysorbate 40 (polyoxyethylen-(20)-sorbitanmonopalmitate), Polysorbate 41, Polysorbate 45, Polysorbate 60 (polyoxyethylen-(20)-sorbitanmonostearate), Polysorbate 61 (polyoxyethylen-(4)-sorbitanmonostearate), Polysorbate 65 (polyoxyethylen-(20)-sorbitantristearate), Polysorbate 80 (polyoxyethylen-(20)-sorbitanmonooleate), Polysorbate 81 (polyoxyethylen-(5)-sorbitanmonooleate), Polysorbate 85 (polyoxyethylen-(20)-sorbitantrioleate), Polysorbate 120 (polyoxyethylen-(20)-sorbitanmonoisostearate), Polysorbate 121, and Polysorbate 125.

Other suitable hydrophilic nonionic surfactants or hydrophilic, nonionic solubilizing agents include long chain alcohols such as the fatty alcohols, cetyl alcohol, stearyl alcohol, and cetostearyl alcohol (consisting predominantly of cetyl and stearyl alcohols), and oleyl alcohol; polyethylene glycol alkyl ethers represented by the formula $CH_3$—$(CH_2)_{10-16}$—$(O$—$C_2H_4)_{1-25}$—$OH$, which includes octaethylene glycol monododecyl ether and pentaethylene glycol monododecyl ether; polypropylene glycol alkyl ethers represented by the formula $CH_3$—$(CH_2)_{10-16}$—$(O$—$C_3H_6)_{1-25}$—$OH$; Glucoside alkyl ethers represented by the formula $CH_3$—$(CH_2)_{10-16}$—$(O$-Glucoside$)_{1-3}$-$OH$, which includes decyl glucoside, lauryl glucoside, and octyl glucoside; polyethylene glycol octylphenyl ethers represented by the formula $C_8H_{17}$—$(C_6H_4)$—$(O$—$C_2H_4)_{1-25}$—$OH$, which includes Triton X-100; polyethylene glycol alkylphenyl ethers represented by the formula $C_9H_{19}$—$(C_6H_4)$—$(O$—$C_2H_4)_{1-25}$—$OH$, which includes Nonoxynol-9; glycerol alkyl esters including glyceryl laurate; polyoxyethylene glycol sorbitan alkyl esters such as the polysorbates identified above; sorbitan alkyl esters; cocamide MEA, cocamide DEA; dodecyldimethylamine oxide; block copolymers of polyethylene glycol and polypropylene glycol including poloxamers; and polyethoxylated tallow amine (POEA).

Component C may be an emulsifier, emollient and solubilizing agent.

The hydrophilic nonionic surfactant or hydrophilic, nonionic solubilizing agent may be present in the composition 14 in amount between about 0.5 wt % to about 7.0 wt %, preferably about 1.0 wt % to about 6.0 wt %, more preferably about 1.0 wt % to about 5.0 wt %, even more preferably about 1.5 wt % to about 5.0 wt %, and still more preferably from about 2.0 wt % to about 5.0 wt %.

In some embodiments, the hydrophilic nonionic surfactant or hydrophilic, nonionic solubilizing agent may be present in the composition 14 in an amount between about 1.0 wt % and about 5.0 wt % or in an amount between about 1.5 wt % and about 5.0 wt % or in an amount between about 2.0 wt % and about 5.0 wt % or in an amount between about 2.5 wt % and about 5.0 wt %.

In some embodiments, the hydrophilic nonionic surfactant or hydrophilic, nonionic solubilizing agent may be present in the composition in an amount less than 5 wt %.

Any of the polysorbates identified herein, or a mixture thereof, may be present in the composition 14 in amount between about 0.5 wt % to about 7.0 wt %, preferably about 1.0 wt % to about 6.0 wt %, more preferably about 1.0 wt % to about 5.0 wt %, even more preferably about 1.5 wt % to about 5.0 wt %, and still more preferably from about 2.0 wt % to about 5.0 wt %.

In some embodiments, any of the polysorbates identified herein, or a mixture thereof, may be present in the composition 14 in an amount between about 1.0 wt % and about 5.0 wt % or in an amount between about 1.5 wt % and about 5.0 wt % or in an amount between about 2.0 wt % and about 5.0 wt % or in an amount between about 2.5 wt % and about 5.0 wt %.

In some embodiments, any of the polysorbates identified herein, or a mixture thereof, may be present in the composition in an amount less than 5 wt %.

Polysorbate 20 may be present in the composition 14 in amount between about 0.5 wt % to about 7.0 wt %, preferably about 1.0 wt % to about 6.0 wt %, more preferably about 1.0 wt % to about 5.0 wt %, even more preferably about 1.5 wt % to about 5.0 wt %, and still more preferably from about 2.0 wt % to about 5.0 wt %.

In some embodiments, Polysorbate 20 may be present in the composition 14 in an amount between about 1.0 wt % and about 5.0 wt % or in an amount between about 1.5 wt % and about 5.0 wt % or in an amount between about 2.0 wt % and about 5.0 wt % or in an amount between about 2.5 wt % and about 5.0 wt %.

In some embodiments, Polysorbate 20 may be present in the composition in an amount less than 5 wt %.

D. Fatty Alcohol Emollient (Component D)

An emollient may be a moisturizer. An emollient makes the external layers of the skin (epidermis) softer and more pliable. An emollient increases the skin's hydration (water content) by reducing evaporation. Emollients may be referred to as a skin-conditioning agent. Component D may be an emulsifying wax.

The present sealant 14 may include an emollient. Alcohols may be emollients. Preferred alcohols include fatty alcohols. Suitable fatty alcohols include cetyl alcohol, stearyl alcohol, cetearyl alcohol, lanolin alcohol, 2-octyl dodecanol, 2-hexyl decanol, hexadecyl alcohol, oleyl alcohol, myristyl alcohol, behenyl alcohol, isostearyl alcohol, or a mixture thereof.

The fatty alcohol is preferably an aliphatic compound. The fatty alcohol that is an aliphatic compound may be cyclic or a straight or branched open-chain compound that contains no rings of any type. The fatty alcohol that is an aliphatic compound can be saturated or unsaturated.

The present fatty alcohols keep the present sealant 14 and its emulsion from separating into its oil and liquid components. The present fatty alcohols may also be used to adjust the thickness of the present sealant 14.

Component D may be an emulsifying wax, spreading agent and sealant agent to minimize loss of moisture from the skin.

The fatty alcohol may be present in the composition 14 in amount between about 0.5 wt % to about 7.0 wt %, preferably about 1.0 wt % to about 6.0 wt %, more preferably about 1.0 wt % to about 5.0 wt %, even more preferably about 1.5 wt % to about 5.0 wt %, and still more preferably from about 2.0 wt % to about 5.0 wt %.

In some embodiments, the fatty alcohol may be present in the composition 14 in an amount between about 1.0 wt % and about 5.0 wt % or in an amount between about 1.5 wt % and about 5.0 wt % or in an amount between about 2.0 wt % and about 5.0 wt % or in an amount between about 2.5 wt % and about 5.0 wt %.

In some embodiments, the fatty alcohol may be present in the composition in an amount less than 5 wt %.

Cetyl alcohol be present in the composition 14 in amount between about 0.5 wt % to about 7.0 wt %, preferably about 1.0 wt % to about 6.0 wt %, more preferably about 1.0 wt % to about 5.0 wt %, even more preferably about 1.5 wt % to about 5.0 wt %, and still more preferably from about 2.0 wt % to about 5.0 wt %.

In some embodiments, cetyl alcohol may be present in the composition 14 in an amount between about 1.0 wt % and about 5.0 wt % or in an amount between about 1.5 wt % and about 5.0 wt % or in an amount between about 2.0 wt % and about 5.0 wt % or in an amount between about 2.5 wt % and about 5.0 wt %.

In some embodiments, cetyl alcohol may be present in the composition in an amount less than 5 wt %.

Stearyl alcohol be present in the composition 14 in amount between about 0.5 wt % to about 7.0 wt %, preferably about 1.0 wt % to about 6.0 wt %, more preferably about 1.0 wt % to about 5.0 wt %, even more preferably about 1.5 wt % to about 5.0 wt %, and still more preferably from about 2.0 wt % to about 5.0 wt %.

In some embodiments, stearyl alcohol may be present in the composition 14 in an amount between about 1.0 wt % and about 5.0 wt % or in an amount between about 1.5 wt % and about 5.0 wt % or in an amount between about 2.0 wt % and about 5.0 wt % or in an amount between about 2.5 wt % and about 5.0 wt %.

In some embodiments, stearyl alcohol may be present in the composition in an amount less than 5 wt %.

E. Humectant (Component E)

The present sealant 14 may include a humectant. A humectant is a substance that attracts or absorbs water. Suitable humectants include a polyalcohol humectant selected from the group of glycerol, propylene glycol, sorbitol, polyethylene glycol, and saccharide; a humectant selected from the group of polypropylene glycols, propylene glycol, butylene glycol, and methyl gluceth-20; a humectant that is a hydrophilic wax such as high molecular weight polyethylene glycols with a molecular weight of from 800 to 20,000 g/mol; a humectant that is a hydrophilic wax such as high molecular weight polyethylene glycols with a molecular weight of from 2000 to 10,000 g/mol; a humectant selected from the group of glycerin, honey, lactic acid, sodium lactate, ceramide, urea, propylene glycol, sorbitol, pyrrolidone carboxylic acid, glycolic acid, gelatin, vitamins, and proteins; a humectant selected from the group of glycerin, lecithin, and propylene glycol; a glycol humectant selected from the group of glycerol, propylene glycol, butylene glycol, dipropylene glycol or diethylene glycol, glycol ethers, such as mono-, di- or tripropylene glycol or mono-, di- or triethylene glycol $(C_1-C_4)$alkyl ethers, and their mixtures; the humectant propylene glycol (1,2-propanediol).

Component E may be a skin softener, skin protectant, and sealing agent to minimize loss of moisture from the skin.

The humectant (Component E) may be present in the composition 14 in amount between about 0.5 wt % to about 7.0 wt %, preferably about 1.0 wt % to about 6.0 wt %, more preferably about 1.0 wt % to about 5.0 wt %, even more preferably about 1.5 wt % to about 5.0 wt %, and still more preferably from about 2.0 wt % to about 5.0 wt %.

In some embodiments, the humectant (Component E) may be present in the composition 14 in an amount between about 1.0 wt % and about 5.0 wt % or in an amount between about 1.5 wt % and about 5.0 wt % or in an amount between about 2.0 wt % and about 5.0 wt % or in an amount between about 2.5 wt % and about 5.0 wt %.

In some embodiments, the humectant (Component E) may be present in the composition in an amount less than 5 wt %.

Propylene glycol may be present in the composition 14 in amount between about 0.5 wt % to about 7.0 wt %, preferably about 1.0 wt % to about 6.0 wt %, more preferably about 1.0 wt % to about 5.0 wt %, even more preferably about 1.5 wt % to about 5.0 wt %, and still more preferably from about 2.0 wt % to about 5.0 wt %.

In some embodiments, propylene glycol may be present in the composition 14 in an amount between about 1.0 wt % and about 5.0 wt % or in an amount between about 1.5 wt % and about 5.0 wt % or in an amount between about 2.0 wt % and about 5.0 wt % or in an amount between about 2.5 wt % and about 5.0 wt %.

In some embodiments, propylene glycol may be present in the composition in an amount less than 5 wt %.

F. Sorbitan Ester Nonionic Surfactant (Component F)

The present sealant 14 may include a sorbitan ester as a nonionic surfactant or emulsifying agent. The nonionic sorbitan ester may be selected from the group of sorbitan stearate, sorbitan laurate, sorbitan sesquioleate, sorbitan oleate, sorbitan tristearate, sorbitan palmitate, sorbitan trioleate, and a sorbitan ester that is a product of sorbitol with a fatty acid selected from stearic acid, lauric acid, oleic acid, and palmitic acid.

Component F may be referred to as a second surfactant component.

Component F may be a sealing agent to minimize loss of moisture from the skin, a skin softener, skin protectant and emulsifier. Component F may include glycerol monostearate or other glycerol esters of stearic acid.

The sorbitan ester nonionic surfactant may be present in the composition 14 in amount between about 0.5 wt % to about 7.0 wt %, preferably about 1.0 wt % to about 6.0 wt %, more preferably about 1.0 wt % to about 5.0 wt %, even more preferably about 1.5 wt % to about 5.0 wt %, and still more preferably from about 2.0 wt % to about 5.0 wt %.

In some embodiments, the sorbitan ester nonionic surfactant may be present in the composition 14 in an amount between about 1.0 wt % and about 5.0 wt % or in an amount between about 1.5 wt % and about 5.0 wt % or in an amount between about 2.0 wt % and about 5.0 wt % or in an amount between about 2.5 wt % and about 5.0 wt %.

In some embodiments, the sorbitan ester nonionic surfactant may be present in the composition in an amount less than 5 wt %.

Sorbitan stearate be present in the composition 14 in amount between about 0.5 wt % to about 7.0 wt %, preferably about 1.0 wt % to about 6.0 wt %, more preferably about 1.0 wt % to about 5.0 wt %, even more preferably about 1.5 wt % to about 5.0 wt %, and still more preferably from about 2.0 wt % to about 5.0 wt %.

In some embodiments, sorbitan stearate may be present in the composition 14 in an amount between about 1.0 wt % and about 5.0 wt % or in an amount between about 1.5 wt % and about 5.0 wt % or in an amount between about 2.0 wt % and about 5.0 wt % or in an amount between about 2.5 wt % and about 5.0 wt %.

In some embodiments, sorbitan stearate may be present in the composition in an amount less than 5 wt %.

G. A Sheatree Derivative (Component G)

The present sealant 14 may include a sheatree derivative selected from the group of *Butyrospermum parkii* (shea) butter, hydrogenated shea butter, *Butyrospermum parkii* (shea) butter unsaponifiables, *Butyrospermum parkii* (shea) butter extract, *Butyrospermum parkii* (shea) oil, *Butyrospermum parkii* (shea) nut extract, and other derivatives of the sheatree. The sheatree is also known as *Butyrospermum parkii*, or *Vitellaria paradoxa*.

Component G may be referred to as a second vegetable oil component or second vegetable oil component mixture.

Component G may be a skin softener, skin protectant, and skin sealant to minimize moisture loss from the skin.

The sheatree derivative may be present in the composition 14 in amount between about 0.5 wt % to about 7.0 wt %, preferably about 1.0 wt % to about 6.0 wt %, more preferably about 1.0 wt % to about 5.0 wt %, even more preferably about 1.5 wt % to about 5.0 wt %, and still more preferably from about 2.0 wt % to about 5.0 wt %.

In some embodiments, the sheatree derivative may be present in the composition 14 in an amount between about 1.0 wt % and about 5.0 wt % or in an amount between about 1.5 wt % and about 5.0 wt % or in an amount between about 2.0 wt % and about 5.0 wt % or in an amount between about 2.5 wt % and about 5.0 wt %.

In some embodiments, the sheatree derivative may be present in the composition in an amount less than 5 wt %.

Shea butter may be present in the composition 14 in amount between about 0.5 wt % to about 7.0 wt %, preferably about 1.0 wt % to about 6.0 wt %, more preferably about 1.0 wt % to about 5.0 wt %, even more preferably about 1.5 wt % to about 5.0 wt %, and still more preferably from about 2.0 wt % to about 5.0 wt %.

In some embodiments, shea butter may be present in the composition 14 in an amount between about 1.0 wt % and about 5.0 wt % or in an amount between about 1.5 wt % and about 5.0 wt % or in an amount between about 2.0 wt % and about 5.0 wt % or in an amount between about 2.5 wt % and about 5.0 wt %.

In some embodiments, shea butter may be present in the composition in an amount less than 5 wt %.

H. Linoleic Acid Component (Component H)

The present sealant may include an oil containing at least 20 wt % of linoleic acid (component H). Suitable oils include grapeseed oil, peanut oil, apricot seed oil, sweet almond oil, hazelnut oil, cottonseed oil, rice bran oil, sesame oil, cherry seed oil, borage oil, rapeseed oil, evening primrose oil, sunflower seed oil, safflower oil, soya oil, wheatgerm oil, passion flower oil, mawseed oil, and linseed oil. For example, these oils may be defined by their acid components, such as oleic, linoleic, palmitic, myristic, and stearic acid. This component H is a vegetable oil that is made up of at least 20 wt % linoleic acid.

Component H is a lubricant. The preferred lubricant is a vegetable oil. A preferred vegetable oil is a seed oil containing at least 20% of linoleic acid. A preferred seed oil is *Prunus Amygdalus Dulcis* (sweet almond) oil.

Component H may be referred to as a third vegetable oil component or third oil component mixture.

Component H may be a skin softener, skin protectant and skin sealant to minimize moisture loss from the skin.

Component H may be present in the composition 14 in amount between about 0.5 wt % to about 7.0 wt %, preferably about 1.0 wt % to about 6.0 wt %, more preferably about 1.0 wt % to about 5.0 wt %, even more preferably about 1.5 wt % to about 5.0 wt %, and still more preferably from about 2.0 wt % to about 5.0 wt %.

In some embodiments, Component H may be present in the composition 14 in an amount between about 1.0 wt % and about 5.0 wt % or in an amount between about 1.5 wt % and about 5.0 wt % or in an amount between about 2.0 wt % and about 5.0 wt % or in an amount between about 2.5 wt % and about 5.0 wt %.

In some embodiments, Component H may be present in the composition in an amount less than 5 wt %.

Sweet almond oil may be present in the composition 14 in amount between about 0.5 wt % to about 7.0 wt %, preferably about 1.0 wt % to about 6.0 wt %, more preferably about 1.0 wt % to about 5.0 wt %, even more preferably about 1.5 wt % to about 5.0 wt %, and still more preferably from about 2.0 wt % to about 5.0 wt %.

In some embodiments, sweet almond oil may be present in the composition 14 in an amount between about 1.0 wt % and about 5.0 wt % or in an amount between about 1.5 wt % and about 5.0 wt % or in an amount between about 2.0 wt % and about 5.0 wt % or in an amount between about 2.5 wt % and about 5.0 wt %.

In some embodiments, sweet almond oil may be present in the composition in an amount less than 5 wt %.

I. Vitamin Antioxidant Component (Component I)

The present sealant 14 may include a vitamin antioxidant component such as beta-carotene (a vitamin A precursor), vitamin C and its derivatives (ascorbyl palmitate, magnesium ascorbyl phosphate, sodium ascorbyl phosphate), vitamin E and its derivatives (alpha-tocopherol, delta-tocopherol, and gamma-tocopherol) and mixtures thereof.

The vitamin component may be fat soluble or water soluble. Fat soluble vitamin components are preferred, such as vitamin A (retinol) and its precursors and derivatives, and vitamin E and its derivatives. Vitamin C is water soluble.

A fat soluble vitamin antioxidant is preferred, such as vitamin A and its precursors and derivatives, and such as vitamin E (tocopherol), and tocopherol derivatives such as an ester of tocopherol, tocopheryl acetate, tocopheryl linoleate, tocopheryl linoleate/oleate, tocopheryl nicotinate, and tocopheryl succinate, potassium ascorbyl tocopheryl phosphate, dioleyl tocopheryl methylsilanol, and tocophersolan.

Component I may be an antioxidant, skin protector and subcutaneous protectant.

Component I may be present in the composition 14 in amount between about 0.01 wt % to about 3.0 wt %, preferably about 0.05 wt % to about 3.0 wt %, more preferably about 0.1 wt % to about 3.0 wt %, even more preferably about 0.2 wt % to about 3.0 wt %, and still more preferably from about 0.3 wt % to about 3.0 wt %.

In some embodiments, Component I may be present in the composition 14 in an amount between about 0.1 wt % and about 4.0 wt % or in an amount between about 0.1 wt % and about 3.0 wt % or in an amount between about 0.1 wt % and about 2.0 wt % or in an amount between about 0.2 wt % and about 2.0 wt %.

In some embodiments, Component I may be present in the composition in an amount less than 2.0 wt %.

Tocopherol or a tocopherol derivative may be present in the composition 14 in amount between about 0.01 wt % to about 3.0 wt %, preferably about 0.05 wt % to about 3.0 wt %, more preferably about 0.1 wt % to about 3.0 wt %, even more preferably about 0.2 wt % to about 3.0 wt %, and still more preferably from about 0.3 wt % to about 3.0 wt %.

In some embodiments, tocopherol or a tocopherol derivative may be present in the composition 14 in an amount between about 0.1 wt % and about 4.0 wt % or in an amount between about 0.1 wt % and about 3.0 wt % or in an amount between about 0.1 wt % and about 2.0 wt % or in an amount between about 0.2 wt % and about 2.0 wt %.

In some embodiments, tocopherol or a tocopherol derivative may be present in the composition in an amount less than 2.0 wt %.

J. Filler (Component J)

The present sealant 14 may include a filler (component J). Suitable fillers may include silica powder; talc; talcum; polyamide particles; polyethylene powders; microspheres based on acrylic copolymers, such as those based on ethylene glycol dimethacrylate/lauryl methacrylate copolymer; expanded powders such as hollow microspheres; powders of natural organic materials such as crosslinked or noncrosslinked corn starch, corn starch, corn starch modified, wheat starch or rice starch, such as the powders of starch crosslinked with octenyl succinate anhydride; silicone resin microbeads; clays (such as bentone, laponite, and saponite) and mixtures thereof.

Component J may be one or more of a opacifying agent, skin protectant, viscosity increasing agent, skin smoothener.

The preferred filler is corn starch or a corn derivative.

Component J may be present in the composition 14 in amount between about 0.01 wt % to about 3.0 wt %, preferably about 0.05 wt % to about 3.0 wt %, more preferably about 0.1 wt % to about 3.0 wt %, even more preferably about 0.2 wt % to about 3.0 wt %, and still more preferably from about 0.3 wt % to about 3.0 wt %.

In some embodiments, Component J may be present in the composition 14 in an amount between about 0.1 wt % and about 4.0 wt % or in an amount between about 0.1 wt % and about 3.0 wt % or in an amount between about 0.1 wt % and about 2.0 wt % or in an amount between about 0.2 wt % and about 2.0 wt %.

In some embodiments, Component J may be present in the composition in an amount less than 2.0 wt %.

Corn starch or a corn derivative may be present in the composition 14 in amount between about 0.01 wt % to about 3.0 wt %, preferably about 0.05 wt % to about 3.0 wt %, more preferably about 0.1 wt % to about 3.0 wt %, even more preferably about 0.2 wt % to about 3.0 wt %, and still more preferably from about 0.3 wt % to about 3.0 wt %.

In some embodiments, corn starch or a corn derivative may be present in the composition 14 in an amount between about 0.1 wt % and about 4.0 wt % or in an amount between about 0.1 wt % and about 3.0 wt % or in an amount between about 0.1 wt % and about 2.0 wt % or in an amount between about 0.2 wt % and about 2.0 wt %.

In some embodiments, corn starch or a corn derivative may be present in the composition in an amount less than 2.0 wt %.

K. Thickening Agents (Component K)

The present sealant 14 may include one or more thickening agents (gelling agents). Component K may have moisturizing, viscosifying, and stabilizing properties. Component K distributes or suspends, or aids in distributing or suspending, an insoluble solid in a liquid. Component K keeps, or aids in keeping, emulsions from separating into their oil and liquid components. Component K controls the consistency and flow of composition 14. Component K has the ability to absorb and retain water. Component K can swell to many times their original volume. Component K may be referred to as a lotion thickener.

Component K may include carboxylic acid polymers, i.e., crosslinked compounds containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol. As to such polymers, U.S. Pat. Nos. 5,087,445, 4,509,949, and 2,798,053 are hereby incorporated by reference in their entireties. Examples of commercially available carboxylic acid polymers suitable herein include carbomers, which are homopolymers of acrylic acid crosslinked with allyl ethers of sucrose or pentaerytritol. Carbomers are available as the Carbopol® 900 series from B.F. Goodrich (e.g., Carbopol® 910, 934, 940, 941, 934P, and 954). Other suitable carboxylic acid polymeric agents include Ultrez® 10 (B.F. Goodrich) and copolymers of C10-C30 alkyl acrylates with one or more monomers of acrylic acid, methacrylic acid, or one of their short chain (i.e., C1-4 alcohol) esters, wherein the crosslinking agent is an allyl ether of sucrose or pentaerytritol. These copolymers are known as acrylates/C10-C30 alkyl acrylate crosspolymers and are commercially available as Carbopol® 1342, Carbopol® 1382, Pemulen TR-1, and Pemulen TR-2, from B.F. Goodrich. In other words, examples of carboxylic acid polymer thickeners suitable herein are those selected from carbomers, acrylates/C10-C30 alkyl acrylate crosspolymers, and mixtures thereof. A carbomer is preferred for component K. A carbomer is an expanded molecule obtained by insertion of a C2 unit in a given molecule. A carbomer is polymer made primarily from acrylic acid.

Component K may include crosslinked polyacrylate polymers. Suitable crosslinked polyacrylate polymers include both cationic and nonionic polymers. As to such, U.S. Pat. Nos. 5,100,660, 4,849,484, 4,835,206, 4,628,078 and 4,599,379 are hereby incorporated by reference in their entireties.

Component K may include polyacrylamide polymers, such as nonionic polyacrylamide polymers including substituted branched or unbranched polyacrylamide polymers. Other polyacrylamide polymers suitable herein include multi-block copolymers of acrylamides and substituted acrylamides with acrylic acids and substituted acrylic acids.

Component K may include polysaccharides. Polysaccharides herein refer to thickening or gelling agents that contain a backbone of repeating sugar (i.e., carbohydrate) units. Suitable nonlimiting examples of polysaccharide thickening agents (gelling agents) include those selected from the group consisting of cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. Further suitable examples include the alkyl-substituted celluloses. Another suitable example includes scleroglucans that include a linear chain of (1-3) linked glucose units with a (1-6) linked glucose every three units.

Component K may include gums, including naturally derived gums. Suitable gums for sealant 14 include acacia, agar, algin, alginic acid, ammonium alginate, amylopectin, calcium alginate, calcium carrageenan, camitine, carrageenan, dextrin, gelatin, gellan gum, guar gum, guar hydroxypropyltrimonium chloride, hectorite, hyaluronic acid, hydrated silica, hydroxypropyl chitosan, hydroxypropyl guar, karaya gum, kelp, locust bean gum, natto gum, potassium alginate, potassium carrageenan, propylene glycol alginate, *sclerotium* gum, sodium carboxymethyl dextran, sodium carrageenan, tragacanth gum, xanthan gum, and mixtures thereof.

Component K may include carboxymethyl cellulose (CMC) or cellulose gum. Carboxymethyl cellulose is a cellulose derivative with carboxymethyl groups (—CH2-COOH) bound to some of the hydroxyl groups of the glucopyranose monomers that make up the cellulose backbone. It is often used as its sodium salt, sodium carboxymethyl cellulose.

Component K may be present in the composition 14 in amount between about 0.01 wt % to about 15.0 wt %, preferably about 0.05 wt % to about 10.0 wt %, more preferably about 0.1 wt % to about 10.0 wt %, even more preferably about 0.2 wt % to about 10.0 wt %, and still more preferably from about 0.3 wt % to about 10.0 wt %.

In some embodiments, Component K may be present in the composition 14 in an amount between about 0.01 wt % and about 5.0 wt % or in an amount between about 0.05 wt % and about 5.0 wt % or in an amount between about 0.1 wt % and about 5.0 wt % or in an amount between about 0.2 wt % and about 5.0 wt %.

In some embodiments, Component K may be present in the composition in an amount less than 2.0 wt %.

A carbomer may be present in the composition 14 in amount between about 0.01 wt % to about 15.0 wt %, preferably about 0.05 wt % to about 10.0 wt %, more preferably about 0.1 wt % to about 10.0 wt %, even more preferably about 0.2 wt % to about 10.0 wt %, and still more preferably from about 0.3 wt % to about 10.0 wt %.

In some embodiments, a carbomer may be present in the composition 14 in an amount between about 0.01 wt % and about 5.0 wt % or in an amount between about 0.05 wt % and about 5.0 wt % or in an amount between about 0.1 wt % and about 5.0 wt % or in an amount between about 0.2 wt % and about 5.0 wt %.

In some embodiments, a carbomer may be present in the composition in an amount less than 2.0 wt %.

A gum may be present in the composition 14 in amount between about 0.01 wt % to about 15.0 wt %, preferably about 0.05 wt % to about 10.0 wt %, more preferably about 0.1 wt % to about 10.0 wt %, even more preferably about 0.2 wt % to about 10.0 wt %, and still more preferably from about 0.3 wt % to about 10.0 wt %.

In some embodiments, a gum may be present in the composition 14 in an amount between about 0.01 wt % and about 5.0 wt % or in an amount between about 0.05 wt % and about 5.0 wt % or in an amount between about 0.1 wt % and about 5.0 wt % or in an amount between about 0.2 wt % and about 5.0 wt %.

In some embodiments, a gum may be present in the composition in an amount less than 2.0 wt %.

Carboxymethyl cellulose or sodium carboxymethyl cellulose may be present in the composition 14 in amount between about 0.01 wt % to about 15.0 wt %, preferably about 0.05 wt % to about 10.0 wt %, more preferably about 0.1 wt % to about 10.0 wt %, even more preferably about 0.2 wt % to about 10.0 wt %, and still more preferably from about 0.3 wt % to about 10.0 wt %.

In some embodiments, carboxymethyl cellulose or sodium carboxymethyl cellulose may be present in the composition 14 in an amount between about 0.01 wt % and about 5.0 wt % or in an amount between about 0.05 wt % and about 5.0 wt % or in an amount between about 0.1 wt % and about 5.0 wt % or in an amount between about 0.2 wt % and about 5.0 wt %.

In some embodiments, carboxymethyl cellulose or sodium carboxymethyl cellulose may be present in the composition in an amount less than 2.0 wt %.

L. Metal Chelator (Component L)

The present sealant 14 may include a metal chelator. Preferred metal chelators include EDTA (ethylenediamine tetraacetic acid) and its salts, calcium disodium EDTA, diammonium EDTA, dipotassium EDTA, disodium EDTA, TEA-EDTA, tetrasodium EDTA, tripotassium EDTA and trisodium EDTA, and the related ingredients HEDTA (hydroxyethyl ethylenediamine triacetic acid) and its trisodium salt, trisodium HEDTA. One or more of these metal chelators may be present in the sealant 14.

Component L may be present in the composition 14 in amount between about 0.01 wt % to about 3.0 wt %, preferably about 0.01 wt % to about 2.0 wt %, more preferably about 0.01 wt % to about 1.5 wt %, even more preferably about 0.01 wt % to about 1.0 wt %, and still more preferably from about 0.01 wt % to about 0.5 wt %.

In some embodiments, Component L may be present in the composition 14 in an amount between about 0.01 wt % and about 2.0 wt % or in an amount between about 0.01 wt % and about 1.9 wt % or in an amount between about 0.01 wt % and about 1.8 wt % or in an amount between about 0.01 wt % and about 1.7 wt %.

In some embodiments, Component L may be present in the composition in an amount less than 2.0 wt %. EDTA, one of its salts, or a mixture thereof may be present in the composition 14 in amount between about 0.01 wt % to about 3.0 wt %, preferably about 0.01 wt % to about 2.0 wt %, more preferably about 0.01 wt % to about 1.5 wt %, even more preferably about 0.01 wt % to about 1.0 wt %, and still more preferably from about 0.01 wt % to about 0.5 wt %.

In some embodiments, EDTA, one of its salts, or a mixture thereof may be present in the composition 14 in an amount between about 0.01 wt % and about 2.0 wt % or in an amount between about 0.01 wt % and about 1.9 wt % or in an amount between about 0.01 wt % and about 1.8 wt % or in an amount between about 0.01 wt % and about 1.7 wt %.

In some embodiments, EDTA, one of its salts, or a mixture thereof may be present in the composition in an amount less than 2.0 wt %.

M. Basic Neutralizing Agents (Component M)

The present sealant 14 may include a pH from about 4.5 to about 10, more preferably from about 4.5 to about 9, and most preferably from about 4.5 to about 8.

Human skin may have a pH of about 4.7 to about 5.5, depending upon the source consulted.

The present sealant 14 may include a basic neutralizing agent. Preferred basic neutralizing agents include sodium hydroxide, calcium hydroxide, magnesium hydroxide and potassium hydroxide, sodium carbonate, sodium hydrogen carbonate, potassium hydroxide, disodium hydrogen phosphate, sodium acetate and mixtures thereof.

The present sealant may be buffered. As to a buffered composition, the Sibley et al. U.S. Pat. No. 5,362,488 entitled Buffered Diaper Rash Cream issued Nov. 8, 1994 is hereby incorporated by reference in its entirety and, further, the Sakuta U.S. Pat. No. 8,828,410 entitled Pasty Composition And Cosmetics Containing The Same issued Sep. 9, 2014 is hereby incorporated by reference in its entirety. A buffer maintains a composition at a certain pH.

Component M may be present in the composition 14 in amount between about 0.01 wt % to about 2.0 wt %, preferably about 0.01 wt % to about 1.9 wt %, more preferably about 0.01 wt % to about 1.8 wt %, even more preferably about 0.01 wt % to about 1.7 wt %, and still more preferably from about 0.01 wt % to about 1.6 wt %.

In some embodiments, component M may be present in the composition 14 in an amount between about 0.01 wt % and about 1.0 wt % or in an amount between about 0.01 wt % and about 0.9 wt % or in an amount between about 0.01 wt % and about 0.8 wt % or in an amount between about 0.01 wt % and about 0.7 wt %.

In some embodiments, component M may be present in the composition in an amount less than 1.0 wt %.

In some embodiments, component M may be added as needed (*Quantum satis*) to attain the desired pH between about 4.5 and about 10.

Sodium hydroxide may be present in the composition 14 in amount between about 0.01 wt % to about 2.0 wt %, preferably about 0.01 wt % to about 1.9 wt %, more preferably about 0.01 wt % to about 1.8 wt %, even more preferably about 0.01 wt % to about 1.7 wt %, and still more preferably from about 0.01 wt % to about 1.6 wt %.

In some embodiments, sodium hydroxide may be present in the composition 14 in an amount between about 0.01 wt % and about 1.0 wt % or in an amount between about 0.01 wt % and about 0.9 wt % or in an amount between about 0.01 wt % and about 0.8 wt % or in an amount between about 0.01 wt % and about 0.7 wt %.

In some embodiments, sodium hydroxide may be present in the composition in an amount less than 1.0 wt %.

In some embodiments, sodium hydroxide may be added as needed (*Quantum satis*) to attain the desired pH between about 4.5 and about 10.

N. Antimicrobial Agent and/or Preservative (Component N)

The present sealant 14 may include an antimicrobial agent and/or preservative. Component N is preferably a formaldehye-donor. Component N is preferably effective against fungi, yeast, and bacteria. One preferred antimicrobial/preservative agent is DMDM hydantoin.

Component N may be present in the composition 14 in amount between about 0.0001 wt % to about 3.0 wt %.

In some embodiments, component N may be present in the composition in an amount less than 0.5 wt %.

In some embodiments, DMDM hydantoin may be present in the composition in an amount less than 0.5 wt %.

As to antimicrobial and/or preservative agents or a combined antimicrobial/preservative agent, the Urgell Beltran et al. U.S. Pat. No. 7,758,851 B2 entitled Preservative Systems And Their Use In Cosmetic Preparations issued Jul. 20, 2010 is hereby incorporated by reference in its entirety.

O. Cream

At room temperature, the present sealant 14 may be in the form of a cream. Creams are viscous liquids or semisolid emulsions, either oil-in-water or water-in-oil. Creams are water-washable, and contain an oil phase, an emulsifier, and an aqueous phase.

P. Lotion

At room temperature, the present sealant 14 may be in the form of a lotion. Lotions are preparations to be applied to the skin surface without friction or with little friction or where friction is minimized, and are typically liquid or semi liquid preparations in which solid particles, including the active agent, are present in a water or alcohol base.

Q. Gels

At room temperature, the present sealant 14 may be a gel. Suitable gels are semisolid, suspension-type systems. Suitable single-phase gels contain organic macromolecules distributed substantially uniformly throughout the carrier liquid, which is typically aqueous, but also, preferably contain an alcohol, and, optionally, an oil. Suitable organic macromolecules, i.e. suitable gelling agents, are cross linked acrylic acid polymers such as the carbomer family of polymers, e.g., carboxypolyalkylenes. Other suitable examples of gels are hydrophilic polymers such as polyethylene oxides, polyoxyethylene-polyoxypropylene copolymers and polyvinylalcohol; cellulosic polymers such as hydroxypropyl cellulose, hydroxyethyl cellulose, hydroxypropyl methylcellulose, hydroxypropyl methylcellulose phthalate, and methyl cellulose; gums such as tragacanth and xanthan gum; sodium alginate; and gelatin. In order to prepare a uniform gel, suitable dispersing agents such as alcohol or glycerin can be added, or the gelling agent can be dispersed by trituration, mechanical mixing or stiffing, or combinations thereof.

R. Ointments

At room temperature, the present sealant 14 may be an ointment. Suitable ointments are semisolid preparations. Suitable ointments are inert, stable, nonirritating, and non-sensitizing. Suitable ointment bases include oleaginous bases, emulsifiable bases, emulsion bases, and water-soluble bases. Suitable oleaginous ointment bases include, for example, vegetable oils. Suitable emulsion ointment bases include water-in-oil (W/O) emulsions and oil-in-water (O/W) emulsions.

S. Pastes

At room temperature, the present sealant 14 may be a paste. A paste is a substance that behaves as a solid until a sufficiently large load or stress is applied, at which point it flows like a fluid. In other words, the present sealant 14 may behave like starch pastes, toothpaste, mustard, and putty, each of which may have a nonflowing state and a flowing state.

T. Emulsions

At room temperature, the present sealant 14 may be an emulsion such as a W/O emulsion, O/W emulsion, O/W/O emulsion, W/O/W emulsions, or microemulsions, where W represents water and O represents oil such as a vegetable oil. The present sealant 14 is preferably a water-in-oil emulsion. As to water/oil and oil/water emulsions, the Stindl U.S. Pat. No. 5,017,605 issued May 21, 1991 and entitled Cosmetic Cream Preparation Containing Water/Oil and Oil/Water Emulsions is hereby incorporated by reference in its entirety. As to a water/oil/water emulsion, the Nadaud et al. U.S. Pat. No. 5,798,108 issued Aug. 25, 1998 and entitled Cosmetic Composition In The Form Of A Water/Oil/Water Triple Emulsion With Gelled External Phase is hereby incorporated by reference it is entirety. As to an oil/water/oil emulsion, the Simon U.S. Pat. No. 6,346,256 B1 issued Feb. 12, 2002 and entitled Stable O/W/O Emulsion And Its Use As A Cosmetic And/Or Dermatological Composition is hereby incorporated by reference in its entirety.

U. Tack and Measurement of Thereof

At room temperature, the present sealant 14 is tacky relative to facial skin and relative to the material from which the mask is formed. This material may be paper, plastic, fabric, cloth, textiles, rubber, elastomer, polymeric, nylon, or a foam. The material from which the mask is formed is a solid.

At room temperature, the present sealant 14 has a tack value of more than or equal to 0.1 N·s, in particular from 0.1 to about 30 N·s; preferably more than or equal to 0.5 N·s, in particular from 0.5 N·s to 20 N·s; better still more than or equal to 0.8 N·s, in particular from 0.8 to 10 N·s; and even better still more than or equal to 1.0, in particular from about 1.0 to about 5.0 N·s.

As to measuring tack value and as to tack value protocol, the following references are hereby incorporated by reference in their entireties: a) the De La Poterie et al. U.S. Patent Application Publication No. US 2005/0191262 A1 published Sep. 1, 2005 and entitled Waxless, Non Rinsed, Cosmetic Keratin Fibre Care Or Makeup Composition, and b) the De La Poterie et al. U.S. Pat. No. 7,887,788 issued Feb. 15, 2011 and entitled Cosmetic Composition Comprising A Tacky Wax.

Components that may have a relatively great impact upon increasing or lowering tack value are component A (water), component B (vegetable oil), fatty alcohol emollient (component D), component J (filler), and component K (thickening or gelling agent).

V. Viscosity and Measurement Thereof

The present sealant 14 has a viscosity at room temperature greater than motor oil or glycerin, which substances may have a viscosity from about 1,000 cps to about 2,000 cps. At room temperature, the present sealant 14 may have a viscosity of about 2000 cps to about 250,000 cps, where honey may have a viscosity of about 2,000 cps to about 3,000 cps, where molasses may have a viscosity of about 5,000 cps to about 10,000 cps, where chocolate syrup may have a viscosity of about 10,000 cps to about 25,000 cps, where table ketchup or table mustard may have a viscosity of about 50,000 cps to about 70,000 cps, where household petroleum jelly has a viscosity of about 60,000 cps to 70,000 cps, and where tomato paste and peanut butter may have a viscosity of about 150,000 cps to about 250,000 cps. Present sealant 14 has a viscosity at room temperature less than household shortening or lard, substances which may have a viscosity of about 1,000,000 cps to about 2,000,000 cps.

At room temperature, the present sealant 14 has a viscosity from about 2000 cps to about 250,000 cps, particularly from about 5000 cps to about 150,000 cps, preferably about 10,000 cps to about 125,000 cps, more preferably from about 25,000 cps to about 100,000 cps, still more preferably from about 30,000 cps to about 95,000 cps, and most preferably from about 35,000 cps to about 90,000 cps, where "cps" means centipoise.

As to measuring viscosity and as to viscosity value protocol, the following references are hereby incorporated by reference in their entireties: a) the De La Poterie et al. U.S. Patent Application Publication No. US 2005/0191262 A1 published Sep. 1, 2005 and entitled Waxless, Non Rinsed, Cosmetic Keratin Fibre Care Or Makeup Composition, and b) the De La Poterie et al. U.S. Pat. No. 7,887,788 issued Feb. 15, 2011 and entitled Cosmetic Composition Comprising A Tacky Wax. For example, viscosity measurements may be taken at room temperature with a Rheomat RM 180 viscometer where a person of ordinary skill in the art can select the spindle for measuring the viscosity on the basis of his or her general knowledge, so as to be able to carry out the measurement of the topical composition 14 tested.

Components that may have a relatively great impact upon increasing or lowering viscosity are component A (water), component B (vegetable oil), fatty alcohol emollient (component D), component J (filler), and component K (thickening or gelling agent).

W. Method of Preparation

Component A (water) is heated to 80° C. Separately the oil portion of sealant 14 is prepared by combining components B to M and then heating this first mixture of components B to M to 80° C. Then component A (water) is added to the mixture of components B to M to form a second mixture. While keeping the second mixture of components A to M at 80° C., the second mixture is mixed thoroughly from about ten to about 30 minutes. Then the second mixture is removed from the heat source and allowed to cool at room temperature to room temperature, whereupon component N (the preservative) is added to form the third and final mixture, the composition or sealant 14, with the third and final mixture being thoroughly mixed from about ten to about 30 minutes. Where used herein, "C." stands for Celsius. Laboratory batch amounts of components A to N may be used.

X. Every Component A Through N not Required

Every component A through N is not required to make the present sealant 14. A number of nonlimiting examples are set out below.

The sheatree derivative (component G) may be eliminated by itself or along with other components.

The inoleic acid (component H) may be eliminated by itself or along with other components.

One of the surfactant components (either component C or component F) may be eliminated by itself or along with other components.

The vitamin antioxidant (component E) may be eliminated by itself or along with other components.

The metal chelator (component L) may be eliminated by itself or along with other components.

One of the surfactant components (either component C or component F), the vitamin antioxidant (component E), and the metal chelator (component L) may be eliminated by themselves or along with other components.

Y. Mixtures within Each of the Components A to N

A component is not necessarily homogenous. For example, the vegetable oil component (component B) may include a mixture of coconut oil and olive oil. The thickening or gelling agent (component K) may include a carbomer and a gum. In other words, each of the components may, by itself, be a mixture of sub-components, where, for instance, one sub-component may be coconut oil and another sub-component may be olive oil. Each of the components may be a mixture of two, three, four or more sub-components.

Z. Hypothetical Example of Topical Composition

A hypothetical composition of the present sealant 14 includes the following components in the following concentrations:

a) purified water (73 wt %);
b) coconut oil (10 wt %);
c) Polysorbate 20 (2.0 wt %);
d) cetyl alcohol (2.0 wt %);
e) propylene glycol (2.0 wt %);
f) sorbitan stearate (2.0 wt %);
g) shea butter (2.0 wt %);
h) sweet almond oil (2.0 wt %);
i) Vitamin E (1.4 wt %);
j) corn starch (1.0 wt %);
k) Carbomer 940 (1.0 wt %);
l) tetrasodium EDTA (1.0 wt %);
m) sodium hydroxide (0.5 wt %); and
n) DMDM hydantoin (0.1 wt %).

The components are then heated, combined, mixed, and cooled according to the process noted above. The viscosity of the end product (present sealant 14) is projected to about 70,000 cps plus or minus about 5000 cps.

AA. Living or Floating Seal

It is preferred that selected components for the present sealant 14 be present in effective amounts to 1) keep the present sealant 14 in a creamy and flowable yet tacky form at room temperature, 2) function as a skin moisturizer 14, 3) stick or tack to human facial skin, 4) stick or tack to one or more of paper and/or plastic and/or cloth and/or fabric and/or textile material of or from which a mask is fabricated, and 5) maintain a living or floating seal 14 between the face confronting peripheral or endless structure of a face mask or respirator and a face. A floating seal is where, at room temperature, the sealant 14 spaces the mask from the skin of the face such that the mask does not rest upon the skin of the face but instead rests upon the sealant 14. The mask, such as the CPAP mask, essentially floats on the sealant 14 that in turn is engaged to the face. When the skin of the face flexes, the sealant 14 moves with the flex, and may "stretch" with the flex such that the sealant 14 remains engaged both to the face and the mask and does not provide an opening through which air can flow in or out of the mask. Tape is not a live or floating seal. An adhesive is not a live or floating seal because, with an adhesive, particularly once the adhesive dries or sets, the mask or skin may separate from the adhesive and thereby form an opening or leak between the mask and the skin. The present sealant 14 when out of a tube and on the face and between the mask and the face remains moist and living and does not dry up at least overnight, at least over an eight hour period (from one minute to eight hours), and, preferably at least over a 10 hour period (from one minute to ten hours), and, even more preferably, at least over a 12 hour period (from one minute to 12 hours), and yet more preferably, at least over a 24 hour period (from one minute to 24 hours). "Remains moist" and "living" and "does not dry up" means to retain at least about 75% by weight of its moisture (water) over the given time period when exposed to the atmosphere at room temperature. While the mask floats, the sealant 14 includes sufficient tacking such that the CPAP mask does not drift such as sideways, transversely, or up or down.

BB. Miscellaneous

One or more of the above components A to N functions as a tackifier, skin moisturizer, viscosity increasing agent, emollient, skin softener, skin protectant, emulsifier, solubilizing agent, emulsifying wax, spreading agent, sealant to minimize evaporation of moisture from the skin, and subcutaneous protectant.

A "derivative" herein is a substance that is derived from another substance: a) by, but not limited to, chemical reactions, b) by, but not limited to, purification processes such as where a component is concentrated to the exclusion of other components, c) by, but not limited to, extraction processes, d) by, but not limited to, sterilization processes, e) by, but not limited to, pasteurization processes, f) by, but not limited to, processes to make the substance fit for a consumer product, and g) by other processes that are not necessarily chemical.

"Room temperature" herein means 70° F.

Thus since the invention disclosed herein may be embodied in other specific forms without departing from the spirit or general characteristics thereof, some of which forms have been indicated, the embodiments described herein are to be considered in all respects illustrative and not restrictive. The scope of the invention is to be indicated by the appended claims, rather than by the foregoing description, and all changes which come within the meaning and range of equivalents of the claims are intended to be embraced therein.

I claim:

1. A method for providing a living seal between a CPAP mask and a human face, the CPAP mask being engaged to a continuous positive airway pressure (CPAP) apparatus, comprising the steps of:
   a) providing a topical composition; then
   b) spreading the topical composition on one of a) a face confronting structure of the CPAP mask and b) a portion of the human face for receiving a face confronting structure of the CPAP mask; then
   c) placing the CPAP mask over at least one of a nose and mouth of a human face; and
   d) selecting the topical composition to include water, the topical composition retaining at least 75% by weight of said water over a time period of 24 hours when exposed to the atmosphere at room temperature.

2. The method of claim 1, and further comprising the step of selecting the topical composition to have a tack value of from about 1.0 N·s to about 5.0 N·s at room temperature.

3. The method of claim 1, and further comprising the step of selecting the topical composition to have a viscosity from about 35,000 cps to about 90,000 cps at room temperature.

4. The method of claim 1, and further comprising the step of selecting the topical composition to include water, a vegetable oil, a hydrophilic nonionic surfactant, a fatty alcohol emollient, a humectant, a sorbitan ester, an oil containing at least 20% wt of linoleic acid, a vitamin antioxidant component, a filler, a thickening agent, a metal chelator, a basic neutralizing agent, and an antimicrobial agent.

5. The method of claim 1, and further comprising the step of selecting the topical composition to include a carbomer.

6. The method of claim 1, and further comprising the step of selecting the topical composition to include a gum.

7. The method of claim 1, and further comprising the step of selecting the topical composition to be one of a cream, lotion, gel, ointment, paste, and emulsion.

8. The method of claim 1, and further comprising the step of selecting the topical composition to be a cream.

9. The method of claim 1, and further comprising the step of selecting the topical composition to be a gel.

10. The method of claim 1 and further comprising the step of selecting the CPAP mask to be a face mask that covers only the mouth.

11. The method of claim 1 and further comprising the step of selecting the CPAP face mask to be a mask that has a portion that is disposed in the mouth.

12. The method of claim 1 and further comprising the step of selecting the CPAP face mask to be a mask that covers only the nose.

13. The method of claim 1 and further comprising the step of selecting the CPAP face mask to be a mask that covers only the mouth and nose.

14. The method of claim 1 and further comprising the step of selecting the CPAP face mask to be a mask that covers the mouth and nose and eyes.

15. The method of claim 1 and further comprising the step of selecting the CPAP face mask to be a mask that includes individual air conduits for each of the nostrils.

16. The method of claim 1 and further comprising the step of selecting the CPAP face mask to be a mask that includes a mouth portion having a peripheral seal about only the mouth and further includes at least one conduit for the nose.

17. The method of claim 1, and further comprising the steps of removing the CPAP mask and subsequently rubbing the topical composition into the skin without washing the face.

18. The method of claim 1, and further comprising the steps of removing the CPAP mask and subsequently washing the face to remove the topical composition.

19. The method of claim 1, and further comprising the step of selecting the topical composition to include:
   a) water in an amount between about 1% wt % and 99% wt %;
   b) a first vegetable oil in an amount between about 1.0 wt % and about 25.0 wt %;
   c) a hydrophilic nonionic first surfactant in an amount between about 0.5 wt % and about 7.0 wt %;
   d) a fatty alcohol emollient in an amount between about 0.5 wt % and about 7.0 wt %;
   e) a humectant in an amount between about 0.5 wt % and about 7.0 wt %;
   f) a second surfactant in an amount between about 0.5 wt % and about 7.0 wt %;
   g) a second vegetable oil in an amount between about 0.5 wt % and about 7.0 wt %;
   h) a third vegetable oil in an amount between about 0.5 wt % and about 7.0 wt %;
   i) a vitamin antioxidant component in an amount between about 0.1 wt % and about 4.0 wt %;
   j) a filler in an amount between about 0.01 wt % and about 3.0 wt %;
   k) a thickening agent in an amount between about 0.01 wt % and about 15.0 wt %;
   l) a metal chelator in an amount between about 0.01 wt % and about 3.0 wt %;
   m) a basic neutralizing agent in an amount between about 0.01 wt % and about 2.0 wt %; and
   n) an antimicrobial agent in an amount between about 0.0001 wt % and about 3.0 wt %.

20. The method of claim 1, and further comprising the step of selecting the topical composition to include:
   a) water in an amount between about 1% wt % and 99% wt %;
   b) a first vegetable oil in an amount between about 1.0 wt % and about 25.0 wt %;
   c) a hydrophilic nonionic first surfactant in an amount between about 0.5 wt % and about 7.0 wt %;
   d) a fatty alcohol emollient in an amount between about 0.5 wt % and about 7.0 wt %;
   e) a humectant in an amount between about 0.5 wt % and about 7.0 wt %;
   f) a second surfactant in an amount between about 0.5 wt % and about 7.0 wt %;
   g) an oil having at least 20 wt % linoleic acid in an amount between about 0.5 wt % and about 7.0 wt %;
   h) a vitamin antioxidant component in an amount between about 0.1 wt % and about 4.0 wt %;
   i) a filler in an amount between about 0.01 wt % and about 3.0 wt %;
   j) a thickening agent in an amount between about 0.01 wt % and about 15.0 wt %;
   k) a metal chelator in an amount between about 0.01 wt % and about 3.0 wt %;
   l) a basic neutralizing agent in an amount between about 0.01 wt % and about 2.0 wt %; and m) an antimicrobial agent in an amount between about 0.0001 wt % and about 3.0 wt %.

21. The method of claim 1, and further comprising the step of selecting the topical composition to include:
   a) coconut oil;
   b) shea butter; and
   c) sweet almond oil.

22. The method of claim 1, and further comprising the step of selecting the topical composition to include water, a vegetable oil, a hydrophilic nonionic surfactant, a fatty alcohol emollient, a humectant, a filler, a thickening agent, a metal chelator, a basic neutralizing agent, and an antimicrobial agent.

23. The method of claim 1, and further comprising the step of selecting the topical composition to include water, a vegetable oil, a filler, and a thickening agent.

24. A method for providing a living seal between a CPAP mask and a human face, the CPAP mask being engaged to a continuous positive airway pressure (CPAP) apparatus, comprising the steps of:
   a) providing a topical composition; then
   b) spreading the topical composition on one of a) a face confronting structure of the CPAP mask and b) a portion of the human face for receiving a face confronting structure of the CPAP mask; then
   c) placing the CPAP mask over at least one of a nose and mouth of a human face; and
   d) selecting the topical composition to include a gum.

25. A method for providing a living seal between a CPAP mask and a human face, the CPAP mask being engaged to a continuous positive airway pressure (CPAP) apparatus, comprising the steps of:
   a) providing a topical composition; then
   b) spreading the topical composition on one of a) a face confronting structure of the CPAP mask and b) a portion of the human face for receiving a face confronting structure of the CPAP mask; then
   c) placing the CPAP mask over at least one of a nose and mouth of a human face; and
   d) selecting the topical composition to include water, a vegetable oil, a filler, and a thickening agent.

* * * * *